(12) United States Patent
Cuttitta et al.

(10) Patent No.: US 7,462,593 B2
(45) Date of Patent: Dec. 9, 2008

(54) COMPOSITIONS AND METHODS FOR PROMOTING ANGIOGENESIS

(76) Inventors: Frank Cuttitta, 7908 Hope Valley Ct., Adamstown, MD (US) 21710; Alfredo Martinez, C/ Enrique Malo, 10, 26144 Galilea, La Rioja (ES); William G. Stetler-Stevenson, 9608 Byeforde Rd., Kensington, MD (US) 20895

( * ) Notice: Subject to any disclaimer, the term of this patent is extended or adjusted under 35 U.S.C. 154(b) by 416 days.

(21) Appl. No.: 10/529,116

(22) PCT Filed: Nov. 7, 2003

(86) PCT No.: PCT/US03/35633

§ 371 (c)(1),
(2), (4) Date: Mar. 24, 2005

(87) PCT Pub. No.: WO2004/043383

PCT Pub. Date: May 27, 2004

(65) Prior Publication Data

US 2006/0160730 A1 Jul. 20, 2006

Related U.S. Application Data

(60) Provisional application No. 60/425,018, filed on Nov. 7, 2002.

(51) Int. Cl.
*A61K 38/00* (2006.01)
(52) U.S. Cl. ............................ 514/2; 514/13
(58) Field of Classification Search ........................ None
See application file for complete search history.

(56) References Cited

U.S. PATENT DOCUMENTS

| | | | |
|---|---|---|---|
| 5,639,855 A | 6/1997 | Kitamura et al. |
| 5,830,703 A | 11/1998 | Kitamura et al. |
| 5,831,004 A | 11/1998 | Campbell et al. |
| 5,837,823 A | 11/1998 | Kitamura et al. |
| 5,910,416 A | 6/1999 | Kitamura et al. |
| 6,117,869 A | 9/2000 | Picard et al. |
| 6,133,304 A | 10/2000 | Peterson, Jr. et al. |
| 6,265,432 B1 | 7/2001 | Purchase, Jr. et al. |
| 6,307,101 B1 | 10/2001 | Campbell et al. |
| 6,320,022 B1 | 11/2001 | Cuttitta et al. |
| 6,339,160 B1 | 1/2002 | Politi et al. |
| 6,350,885 B1 | 2/2002 | O'Brien et al. |
| 6,440,421 B1 | 8/2002 | Cornish et al. |
| 2002/0055615 A1 | 5/2002 | Cuttitta et al. |

FOREIGN PATENT DOCUMENTS

| | | |
|---|---|---|
| EP | 0 845 036 | 6/1999 |
| EP | 0 926 238 A2 | 11/2000 |
| EP | 0 926 238 A3 | 11/2000 |
| WO | WO 97/07214 | 2/1997 |
| WO | WO 01/18550 | 3/2001 |
| WO | WO 2004/032708 | 4/2004 |

OTHER PUBLICATIONS

Ginda et al., "Decrease of TSH Levels and Epithelium/Colloid Ratio in Rat Thyroid Glands Following Administration of Proadrenomedullin N-Terminal Peptide (12-20)," *Horm. Metab. Res.*, 32:10-14, 2000.
Belloni et al., "Proadrenomedullin N-Terminal 20 Peptide (PAMP), Acting Through PAMP(12-20)-Sensitive Receptors, Inhibits $Ca^{2+}$-Dependent, Agonist-Stimulated Secretion of Human Adrenal Glands," *Hypertension* 33:1185-1189 (1999).
Calvo et al., "Adrenomedullin and proadrenomedullin N-terminal 20 peptide in the normal prostate and in prostate carcinoma," *Microsc. Res. Tech.* 57(2):98-104 (Apr. 2002) Abstract Only.
Champion et al., "Proadrenomedullin NH2-termainal 20 peptide has direct vasodilator activity in the cat," *Am J. Physiol.* 272(4 Pt 2):R1047-54 (Apr. 1997) Abstract Only.
Champion et al., "Structure-activity relationships of adrenomedullin in the circulation and adrenal gland," *Regul. Peptides* 85(1):1-8 (Nov. 30, 1999). Abstract Only.
Champion et al., "Tone-dependent vasodilator responses to proadrenomedullin NH2-terminal 20 peptide in the hindquarters vascular bed of the rat," *Peptides* 18(4):513-519 (1997) Abstract Only.
Corcoran et al., "MMP-2: Expression, Activation and Inhibition," *Enzyme Protein* 49:7-19 (1996).
Corti et al., "Vasopeptidase Inhibitors: A New Therapeutic Concept in Cardiovascular Disease," *Cardiovascular Drugs* 104:1856-1862 (Oct. 9, 2001).
Eto et al., "Adrenomedullin and proadrenomedullin N-terminal 20 peptide: vasodilatory peptides with multiple cardiovascular and endocrine actions," *Trends in Endo and Metab.* 12(3):91-93 (Apr. 1, 2001) Abstract Only.
Fernandez-Patron, "Vascular Matrix Metalloproteinase-2-Dependent Cleavage of Calcionin Gene-Related Peptide Promotes Vasoconstriction," *Circ Res.* 87:670-676 (2000).
Fry et al., "Proadrenomedullin NH2-terminal peptide (PAMP) (12-20) has vasodepressor activity in the rat and cat," *Life Science* 60(10):PL161-167 (1997) Abstract Only.
Giannelli and Antonaci, "Gelantinases and their inhibitors in tumor metastasis: form biological research to medical applications," *Histol Histopathol* 17:339-345 (2002).
Goffin et al., "Human Endometrial Epithelial Cells Modulate the Activation of Gelatinase A by Stromal Cells," *Gynecol Obstet Invest* 53:105-111 (2002).
Ishimitsu et al. "Genomic structure of human adrenomedullin gene," *Biochem Biophys Res Commun* 203(1):631-639 (Aug. 30, 1994) Abstract Only.
Kangawa et al., "Adrenomedullin: a new hypotensive peptide," *J. Hypertens Suppl.* 14(5):S105-110 (Dec. 1996) Abstract Only.
Kapas et al., "Regulation of PAMP and adrenomedullin receptor expression in the rat adrenal zona glomerulosa" *Endoc Res.* 24(3-4):717-20 (Aug.-Nov. 1998) Abstract Only.
Kitamura et al., "Adrenomedullin: a novel hypotensive peptide isolated from human pheochromocytoma," *Biochem Biophys Res Commun* 192(2):553-560 (Apr. 30, 1993).

(Continued)

*Primary Examiner*—Christine J Saoud
(74) *Attorney, Agent, or Firm*—Klarquist Sparkman, LLP

(57) ABSTRACT

The present disclosure concerns the use of peptides and compositions, such as pharmaceutical compositions, to influence angiogenesis. Particular methods are useful for promoting angiogenesis, while others are particularly useful for inhibiting angiogenesis.

10 Claims, 8 Drawing Sheets

OTHER PUBLICATIONS

Kitamura et al., "Cloning and characterization of cDNA encoding a precursor for human adrenomedullin," *Biochem Biophys Res Commun* 194(2):720-725 (Jul. 30, 1993) *Abstract Only*.

Kitamura et al., "Identification and hypotensive activity of proadrenomedullin N-terminal 20 peptide (PAMP)," *FEBS Letters* 351(1):35-7 (Aug. 29, 1994) *Abstract Only*.

Kleiner and Stetler-Stevenson, "Matrix metalloproteinases and metastasis," *Cancer Chemother Pharmacol* 43(Suppl):S42-S51 (1999).

Kugler, "Matrix Metalloproteinases and their Inhibitors," *Anticancer Research* 19:1589-1592 (1999).

Kuwasako et al., "Increased plasma proadrenomedullin N-terminal 20 peptide in patients with essential hypertension," *Ann Clin Biochem.* 36:(pt5):622-628 (Sep. 1999) *Abstract Only*.

Lewis et al., "Degradation of human adrenomedullin (1-52) by plasma membrane enzymes and identification of metabolites," *Peptides* 18(5):733-739 (1997).

Makino et al., "Attenuated hypotensive response to proadrenomedullin N-terminal 20 peptide in pregnant rats: modulation by steroid hormones," *Peptides* 20(12):1521-1525 (1999) *Abstract Only*.

Matsui et al., "Biosynthesis and Secretion of Adrenomedullin and Proadrenomedullin N-Terminal 20 Peptide in a Rat Model of Endotoxin Shock," *Hypertens* 24:543-549 (2001).

Matsui et al., "Lack of hypotensive effect of chronically infused proadrenomedullin N-terminal 20 peptide in rats," *Horm Metab Res* 30(9):555-6 (1998) *Abstract Only*.

Martínez et al., "Proadrenomedullin $NH_2$- Terminal 20 Peptide is a Potent Angiogenic Factor, and its Inhibition Results in Reduction of Tumor Growth," *Cancer Res* 64:6489-6496 (Sep. 15, 2004).

Martínez et al. "The Effects of Adrenomedulling Overexpression in Breast Tumor Cells," *J. Nat. Cancer Inst.* 94(16):12 pages (Aug. 21, 2002).

Moody et al., "Adrenomedullin binds with high affinity, elevates cyclic AMP, and stimulates c-fos mRNA in C6 glioma cells," *Peptides* 18(8):1111-1115 (1997) *Abstract Only*.

Nakamura et al. "Comparison of vasodilator potency of adrenomedullin and proadrenomedullin N-terminal 20 peptide in human," *Life Sci.* 65(20):2151-2156 (1999) *Abstract Only*.

Nossaman et al., "Effects of Phentolamine on Responses to PAMP in the Hindquarters Vascular Bed of the Rat," *J. Cardiovasc. Pharmacol Ther.* 2(3):153-157 (Jul. 1997) *Abstract Only*.

Robert et al., "Differential regulation of matrix metalloproteinases associated with aging and hypertension in the rat heart," *Lab Invest.* 76(5):729-738 (May 1997) *Abstract Only*.

Saita et al., "Cardiovascular and sympathetic effects of proadrenomedullin NH2-terminal 20 peptide in conscious rats," *Regul Pept* 77(1-3):147-153 (Oct. 16, 1998) *Abstract Only*.

Samson et al., "Central mechanisms for the hypertensive effects of preproadrenomedullin-derived peptides in conscious rats," *Am J. Physiol* 274:R1505-R1509 (1998).

Samson, "Proadrenomedullin-derived peptides," *Front Neuroendocrinol.* 19(2):100-27 (Apr. 1998) *Abstract Only*.

Shimosawa et al., "A Newly Identified Peptide, Proadrenomedullin N-Terminal 20 Peptide, Induces Hypotensive Action via Pertussis Toxin-Sensitive Mechanisms," *Hypertension* 30:1009-1014 (1997).

Shimosawa et al., "Adrenomedullin, an Endogenous Peptide, Counteracts Cardiovascular Damage," *Circulation* 105:106-111 (2002).

Shimosawa and Fujito, "Hypotensive Effect of a Newly Identified Peptide, Proadrenomedullin N-Terminal 20 Peptide," *Hypertension* 28:325-329 (1996).

Uemura et al., "Aldosterone augments adrenomedullin production without stimulating pro-adrenomedullin N-terminal 20 peptide secretion in vascular smooth muscle cells," *J. Hypertens.* 20(6):1209-1214 (Jun. 2002) *Abstract Only*.

Watanabe et al., "Vasopressor activity of N-terminal fragments of adrenomedullin in anesthetized rat," *Biochem. Biophys. Res. Comm.* 219:59-63 (1996).

Wilkinson et al., "Adrenomedullin (ADM) in the human forearm vascular bed: effect of neutral endopeptidase inhibition and comparison with proadrenomedullin $NH_2$-terminal 20 peptide (PAMP)," *J. Clin Pharm* 52:159-164 (2001).

Zhao et al., "PCR display identifies tamoxifen induction of the novel aniogenic factor adrenomedullin by a non estrogenic mechanism in the human endometrium," *Oncogene* 16(3):409-415 (Jan. 22, 1998) *Abstract Only*.

SEQUENCE LISTING

```
<160> NUMBER OF SEQ ID NOS: 20

<210> SEQ ID NO 1
<211> LENGTH: 1449
<212> TYPE: DNA
<213> ORGANISM: Homo sapiens
<220> FEATURE:
<221> NAME/KEY: CDS
<222> LOCATION: (157)..(714)

<400> SEQUENCE: 1
ctggatagaa cagctcaagc cttgccactt cgggcttctc actgcagctg ggcttggact      60
tcggagtttt gccattgcca gtgggacgtc tgagactttc tccttcaagt acttggcaga     120
tcactctctt agcagggtct gcgcttcgca gccggg atg aag ctg gtt tcc gtc      174
                                         Met Lys Leu Val Ser Val
                                          1               5 gcc ctg atg tac ctg ggt tcg ctc gcc ttc cta ggc gct gac acc gct      222
Ala Leu Met Tyr Leu Gly Ser Leu Ala Phe Leu Gly Ala Asp Thr Ala
            10                  15                  20 cgg ttg gat gtc gcg tcg gag ttt cga aag aag tgg aat aag tgg gct      270
Arg Leu Asp Val Ala Ser Glu Phe Arg Lys Lys Trp Asn Lys Trp Ala
        25                  30                  35 ctg agt cgt ggg aag agg gaa ctg cgg atg tcc agc agc tac ccc acc      318
Leu Ser Arg Gly Lys Arg Glu Leu Arg Met Ser Ser Ser Tyr Pro Thr
    40                  45                  50 ggg ctc gct gac gtg aag gcc ggg cct gcc cag acc ctt att cgg ccc      366
```

| | | |
|---|---|---|
| Gly Leu Ala Asp Val Lys Ala Gly Pro Ala Gln Thr Leu Ile Arg Pro<br>55                   60                  65                  70 | |
| cag gac atg aag ggt gcc tct cga agc ccc gaa gac agc agt ccg gat<br>Gln Asp Met Lys Gly Ala Ser Arg Ser Pro Glu Asp Ser Ser Pro Asp<br>              75                  80                  85 | 414 |
| gcc gcc cgc atc cga gtc aag cgc tac cgc cag agc atg aac aac ttc<br>Ala Ala Arg Ile Arg Val Lys Arg Tyr Arg Gln Ser Met Asn Asn Phe<br>            90                  95                 100 | 462 |
| cag ggc ctc cgg agc ttt ggc tgc cgc ttc ggg acg tgc acg gtg cag<br>Gln Gly Leu Arg Ser Phe Gly Cys Arg Phe Gly Thr Cys Thr Val Gln<br>         105                  110                115 | 510 |
| aag ctg gca cac cag atc tac cag ttc aca gat aag gac aag gac aac<br>Lys Leu Ala His Gln Ile Tyr Gln Phe Thr Asp Lys Asp Lys Asp Asn<br>     120                 125                130 | 558 |
| gtc gcc ccc agg agc aag atc agc ccc cag ggc tac ggc cgc cgg cgc<br>Val Ala Pro Arg Ser Lys Ile Ser Pro Gln Gly Tyr Gly Arg Arg Arg<br>135                  140                145              150 | 606 |
| cgg cgc tcc ctg ccc gag gcc ggc ccg ggt cgg act ctg gtg tct tct<br>Arg Arg Ser Leu Pro Glu Ala Gly Pro Gly Arg Thr Leu Val Ser Ser<br>               155                160              165 | 654 |
| aag cca caa gca cac ggg gct cca gcc ccc ccg agt gga agt gct ccc<br>Lys Pro Gln Ala His Gly Ala Pro Ala Pro Pro Ser Gly Ser Ala Pro<br>     170                 175                180 | 702 |
| cac ttt ctt tag gatttaggcg cccatggtac aaggaatagt cgcgcaagca<br>His Phe Leu<br>     185 | 754 |
| tcccgctggt gcctcccggg acgaaggact tcccgagcgg tgtggggacc gggctctgac | 814 |
| agccctgcgg agaccctgag tccgggaggc accgtccggc ggcgagctct ggctttgcaa | 874 |
| gggcccctcc ttctggggc ttcgcttcct tagccttgct caggtgcaag tgccccaggg | 934 |
| ggcggggtgc agaagaatcc gagtgtttgc caggcttaag gagaggagaa actgagaaat | 994 |
| gaatgctgag accccggag cagggggtctg agccacagcc gtgctcgccc acaaactgat | 1054 |
| ttctcacggc gtgtcacccc accagggcgc aagcctcact attacttgaa ctttccaaaa | 1114 |
| cctaaagagg aaaagtgcaa tgcgtgttgt acatacagag gtaactatca atatttaagt | 1174 |
| ttgttgctgt caagattttt tttgtaactt caaatataga gatattttg tacgttatat | 1234 |
| attgtattaa gggcatttta aaagcaatta tattgtcctc ccctatttta agacgtgaat | 1294 |
| gtctcagcga ggtgtaaagt tgttcgccgc gtggaatgtg agtgtgtttg tgtgcatgaa | 1354 |
| agagaaagac tgattacctc ctgtgtggaa gaaggaaaca ccgagtctct gtataatcta | 1414 |
| tttacataaa atgggtgata tgcgaacagc aaacc | 1449 |

<210> SEQ ID NO 2
<211> LENGTH: 185
<212> TYPE: PRT
<213> ORGANISM: Homo sapiens

<400> SEQUENCE: 2

Met Lys Leu Val Ser Val Ala Leu Met Tyr Leu Gly Ser Leu Ala Phe
1                 5                    10                   15

Leu Gly Ala Asp Thr Ala Arg Leu Asp Val Ala Ser Glu Phe Arg Lys
                20                    25                   30

Lys Trp Asn Lys Trp Ala Leu Ser Arg Gly Lys Arg Glu Leu Arg Met
             35                    40                   45

Ser Ser Ser Tyr Pro Thr Gly Leu Ala Asp Val Lys Ala Gly Pro Ala
50                  55                    60

-continued

```
Gln Thr Leu Ile Arg Pro Gln Asp Met Lys Gly Ala Ser Arg Ser Pro
 65                  70                  75                  80

Glu Asp Ser Ser Pro Asp Ala Ala Arg Ile Arg Val Lys Arg Tyr Arg
                 85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Arg Ser Lys Ile Ser Pro Gln
    130                 135                 140

Gly Tyr Gly Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185
```

```
<210> SEQ ID NO 3
<211> LENGTH: 60
<212> TYPE: DNA
<213> ORGANISM: Homo sapiens
<220> FEATURE:
<221> NAME/KEY: CDS
<222> LOCATION: (1)..(60)

<400> SEQUENCE: 3 gct cgg ttg gat gtc gcg tcg gag ttt cga aag aag tgg aat aag tgg      48
Ala Arg Leu Asp Val Ala Ser Glu Phe Arg Lys Lys Trp Asn Lys Trp
  1               5                  10                  15 gct ctg agt cgt                                                     60
Ala Leu Ser Arg
            20
```

```
<210> SEQ ID NO 4
<211> LENGTH: 20
<212> TYPE: PRT
<213> ORGANISM: Homo sapiens

<400> SEQUENCE: 4

Ala Arg Leu Asp Val Ala Ser Glu Phe Arg Lys Lys Trp Asn Lys Trp
  1               5                  10                  15

Ala Leu Ser Arg
            20
```

```
<210> SEQ ID NO 5
<211> LENGTH: 27
<212> TYPE: DNA
<213> ORGANISM: Homo sapiens
<220> FEATURE:
<221> NAME/KEY: CDS
<222> LOCATION: (1)..(27)

<400> SEQUENCE: 5 aag tgg aat aag tgg gct ctg agt cgt                                 27
Lys Trp Asn Lys Trp Ala Leu Ser Arg
  1               5
```

```
<210> SEQ ID NO 6
<211> LENGTH: 9
<212> TYPE: PRT
<213> ORGANISM: Homo sapiens

<400> SEQUENCE: 6
```

```
Lys Trp Asn Lys Trp Ala Leu Ser Arg
1               5
```

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 7
acatgaaggg tgcctctcga a           21

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 8
aggccctgga agttgttcat g           21

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 9
tcagagcgga gaaagcattt gt          22

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 10
tcggcttgtc acatctgcaa            20

<210> SEQ ID NO 11
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 11
cgaccctcac atcaagctac aac         23

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 12
ccagttcgtt tcagtgccac at          22

<210> SEQ ID NO 13
<211> LENGTH: 21

```
<212> TYPE: DNA
<213> ORGANISM: Artificial Sequence
<220> FEATURE:
<223> OTHER INFORMATION: Oligonucleotide primer

<400> SEQUENCE: 13
ttcggaggaa gagaagcatc g                                          21

<210> SEQ ID NO 14
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 14
gcacttgaca ctgctcgtgt tg                                         22

<210> SEQ ID NO 15
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 15
aacaaccgca acgtgcagt                                             19

<210> SEQ ID NO 16
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 16
tctcgatctt tctcacctgg ac                                         22

<210> SEQ ID NO 17
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 17
ttgaggaacc cagtgatgga ac                                         22

<210> SEQ ID NO 18
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 18
cagcttctgt gaattgtggc at                                         22

<210> SEQ ID NO 19
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 19
```

```
atgctcttag ctgagtgtcc cg                                          22
```

<210> SEQ ID NO 20
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 20

```
attcctagct gcggtatcca gg                                          22
```

COMPOSITIONS AND METHODS FOR PROMOTING ANGIOGENESIS

CROSS REFERENCE TO RELATED APPLICATIONS

This is a § 371 U.S. national stage of PCT/US2003/035633, filed Nov. 7, 2003, which was published in English under PCT Article 2(2), and claims the benefit of U.S. Provisional Application No. 60/425,018, filed Nov. 7, 2002. Both applications are incorporated herein in their entirety.

FIELD

The present disclosure concerns the use of peptides and compositions, such as pharmaceutical compositions, to influence angiogenesis. Particular methods are useful for promoting angiogenesis, while others are particularly useful for inhibiting angiogenesis.

BACKGROUND

Angiogenesis, the process of developing a hemovascular network from pre-existing blood vessels, is essential for the growth of solid tumors and is a component of normal wound healing and growth processes. It also has been implicated in the pathophysiology of many diseases and conditions, including atherogenesis, arthritis, psoriasis, corneal neovascularization, and diabetic retinopathy.

The molecular messengers responsible for the process of angiogenesis have long been sought. For example, a variety of soluble mediators have been implicated in the induction of neovascularization. These include prostaglandins (Auerbach, in *Lymphokines,* Pick and Landy, eds., 69-88, Academic Press, New York, 1981), human urokinase (Berman et al., *Invest. Opthalm. Vis. Sci.* 22: 191-199, 1982), copper (Raju et al., *J. Natl. Cancer Inst.* 69: 1183-1188, 1982), and various "angiogenesis factors" (for instance, see U.S. Pat. No. 4,916,073). The most often cited angiogenic growth factors are basic fibroblast growth factor (bFGF) and vascular endothelial growth factor (VEGF).

Because angiogenesis factors play an important role in wound healing (Rettura et al., FASEB Abstract #4309, 61st Annual Meeting, Chicago, 1977) and the development of malignancies (Klagsburn et al., *Cancer Res.* 36: 110-114, 1976; and Brem et al., Science 195: 880-881, 1977), it would be advantageous to identify new angiogenic and anti-angiogenic agents.

SUMMARY OF THE DISCLOSURE

The present disclosure takes advantage of the discovery that, in addition to its hypotensive and vasodilatory effects, proadrenomedullin N-terminal 20 peptide (PAMP), a 20 amino-acid molecule originating from the post-translational processing of pre-proadrenomedullin, functions as a potent angiogenic factor. When compared to other known angiogenic factors, such as vascular endothelial growth factor (VEGF) and basic fibroblast growth factor (bFGF), PAMP is estimated to be one million times more potent on a molar basis.

Described herein are methods of inducing angiogenesis in a tissue. The methods include introducing into the tissue an effective amount of SEQ ID NO: 4 or a variant or fragment thereof that has at least 90% sequence identity with SEQ ID NO: 4 and that retains angiogenic activity, thereby inducing angiogenesis in the tissue.

Also described is a method of promoting angiogenesis in a target area in a subject where angiogenesis is desired. The method includes introducing into the target area a therapeutically effective amount of SEQ ID NO: 4 or a variant or fragment thereof that has at least 90% sequence identity with SEQ ID NO: 4 and that retains angiogenic activity, thereby promoting angiogenesis in the target area in the subject.

Further embodiments are SEQ ID NO: 4 or a variant or fragment thereof that has at least 90% sequence identity with SEQ ID NO: 4 and that retains angiogenic activity, for use in a pharmaceutical composition for inducing angiogenesis, for use in treating coronary artery disease, for use in treating peripheral vascular disease, and for use in treating wounds.

Still further embodiments are kits for inducing angiogenesis in a tissue in a subject. The kits include a container and an amount of SEQ ID NO: 4 or a variant or fragment thereof that has at least 90% sequence identity with SEQ ID NO: 4 and that retains angiogenic activity.

Also described herein are methods of inhibiting angiogenesis in a tissue wherein the formation of new blood vessels is not desired, which methods involve introducing into the tissue an effective amount of an inhibitor of proadrenomedullin N-terminal 20 peptide (PAMP), thereby inhibiting angiogenesis in the tissue.

Also described are methods of inhibiting angiogenesis in a target area in a subject where inhibition of angiogenesis is desired. The methods include introducing a therapeutically effective amount of a proadrenomedullin N-terminal 20 peptide (PAMP) inhibitor to the target area, thereby inhibiting angiogenesis in the subject.

Further embodiments are proadrenomedullin N-terminal 20 peptide (12-20) preparations for use in a pharmaceutical composition for inhibiting angiogenesis, for use in treating a tumor, for use in treating retinopathy, for use in treating retinopathy, for use in treating endometriosis, for use in treating arthritis, and for use in treating psoriasis.

Also described herein is a kit for inhibiting angiogenesis in a tissue in a subject. In some embodiments, the kit includes a container and an amount of proadrenomedullin N-terminal 20 peptide (12-20).

Still further embodiments are methods of screening for an inhibitor of proadrenomedullin N-terminal 20 peptide (PAMP). The method includes screening a library of small molecules for disruption of the binding of anti-PAMP antibody to PAMP, and screening a molecule identified as disrupting the binding of anti-PAMP antibody to PAMP for anti-angiogenesis activity in an angiogenesis bioassay.

The foregoing and other features and advantages will become more apparent from the following detailed description of several embodiments, which proceeds with reference to the accompanying figures.

BRIEF DESCRIPTION OF THE FIGURES

(FIG. 4A-F) Digital images of the angioreactors still attached to the skin at the end of the experiment. The new blood vessels can be seen growing from the tube opening. The capsules contain PBS as a negative control (FIG. 4A), 7 µM bFGF as a positive control (FIG. 4B), $10^{-15}$ M PAMP (FIG. 4C), $10^{-13}$ M PAMP (FIG. 4D), $10^{-11}$ M PAMP (FIG. 4E), or $10^{-9}$ M PAMP (FIG. 4F). Bar=2.0 mm. The matrigel plugs were digested with dispase and the FITC-dextran contents were measured to quantify the volume of blood circulating through the implants (FIG. 4G). Each bar represents the mean and standard deviation of 6 independent values. Statistically significant differences between implants treated with PAMP and VEGF at the same concentration are represented by asterisks. *: $p<0.05$; : $0.01>p>0.001$; *: $p<0.001$

(FIG. 6A) Human microvascular endothelial cells were seeded in 96 well plates in the presence of increasing concentrations of the angiogenic peptides in serum-free medium. After three days in culture, the number of viable cells was estimated by an MTT assay and expressed as percent growth over untreated controls. Each point represents the mean and standard deviation of eight independent measurements. (FIG. 6B) The same cells were seeded in the upper chamber of a ChemoTx microplate coated with fibronectin where different concentrations of the peptides had been placed in the lower chambers. Each point represents the mean and standard deviation of four independent measurements. (FIG. 6C) Endothelial cells were seeded over a layer of solidified matrigel in the presence of different concentrations of angiogenic peptides. The complexity of the cord network was estimated by the number of knots per microscopic field. Each bar represents the mean and standard deviation of 3 independent wells. Asterisks represent statistically significant differences with the untreated cells. *: $p<0.05$; : $0.01p>0.001$; *: $p<0.001$. (FIG. 6D) The same cells were exposed to 10 nM PAMP overnight and their contents in angiogenic molecule's mRNA were measured by real-time PCR. Each bar represents the ratio between the gene of interest in the treated cells and the contents in the untreated cells. The horizontal line indicates no change over untreated conditions.

(FIG. 7B) PAMP(12-20) was also able to inhibit the angiogenesis induced by two human lung cancer tumor cells embedded in the matrigel capsules. PAMP(12-20) was added at 100 nM. Each bar represents the mean and standard deviation of six independent measurements. Statistical differences with untreated cells are represented as * ($p<0.05$).

SEQUENCE LISTING

Figure 1:
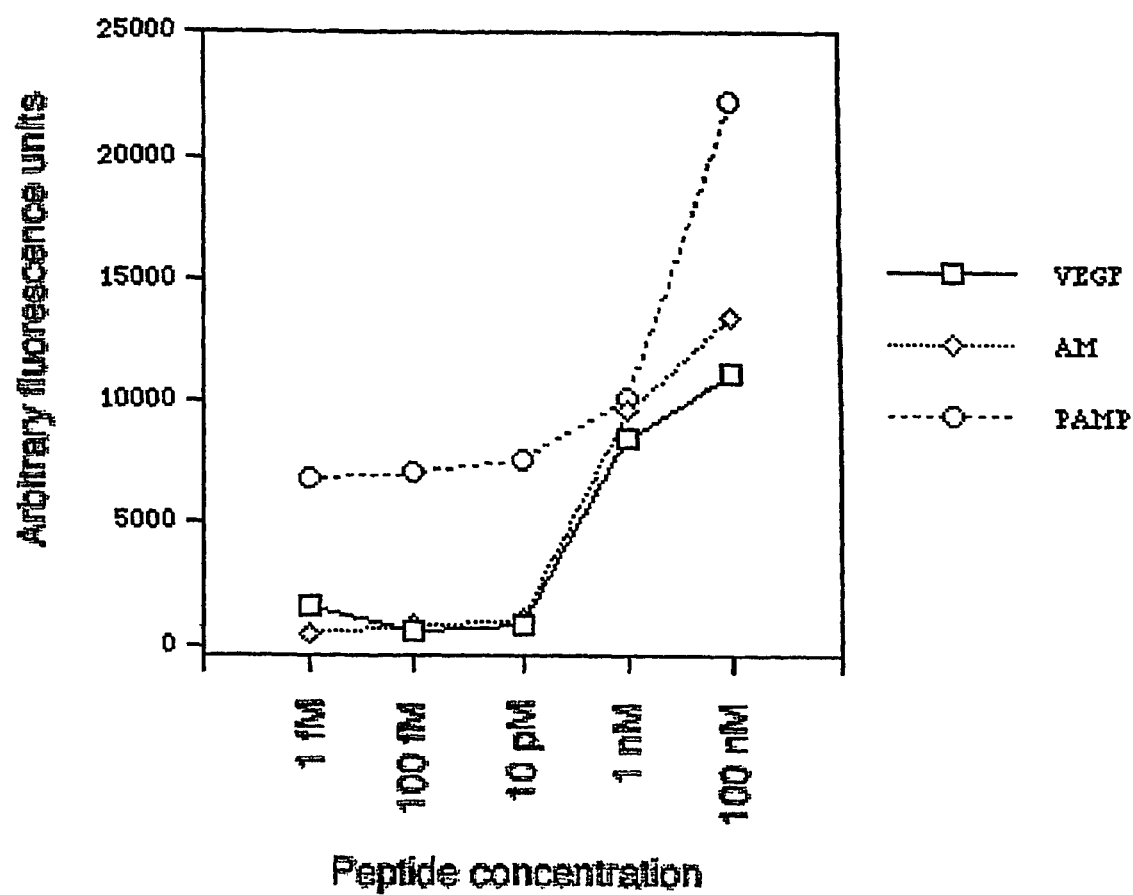
FIG. 1 is a graph showing that PAMP promotes angiogenesis in a DIVAA assay.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO 1 is the nucleotide sequence that encodes preproadrenomedullin.

SEQ ID NO 2 is the protein sequence of preproadrenomedullin.

SEQ ID NO 3 is the nucleotide sequence that encodes proadrenomedullin N-terminal 20 peptide (PAMP).

SEQ ID NO 4 is the protein sequence of proadrenomedullin N-terminal 20 peptide (PAMP).

SEQ ID NO 5 is the nucleotide sequence that encodes proadrenomedullin N-terminal 20 peptide (12-20).

SEQ ID NO 6 is the protein sequence of proadrenomedullin N-terminal 20 peptide (12-20).

SEQ ID NO 7 is the AM forward primer.
SEQ ID NO 8 is the AM reverse primer.
SEQ ID NO 9 is the VEGF forward primer.
SEQ ID NO 10 is the VEGF reverse primer.
SEQ ID NO 11 is the bFGF forward primer.
SEQ ID NO 12 is the bFGF reverse primer.
SEQ ID NO 13 is the PGDF A forward primer.
SEQ ID NO 14 is the PGDF A reverse primer.
SEQ ID NO 15 is the PDGF B forward primer.
SEQ ID NO 16 is the PDGF B reverse primer.
SEQ ID NO 17 is the PDGF C forward primer.
SEQ ID NO 18 is the PDGF C reverse primer.
SEQ ID NO 19 is the 18 S RNA forward prier.
SEQ ID NO 20 is the 18 5 RNA reverse primer.

DETAILED DESCRIPTION

I. Abbreviations aFGF: acidic fibroblast growth factor
bFGF: basic fibroblast growth factor
CABG: coronary artery bypass graft surgery
GLP-1: glucagon-like peptide-1
IL-8: interleukin-8
KLH: keyhole limpet hemocyanin
MMP2: metalloproteinase 2
MMP9: metalloproteinase 9
PAMP: proadrenomedullin N-terminal 20 peptide
PBS: phosphate buffered saline
PTCA: percutaneous transluminal coronary angioplasty
PVD: peripheral vascular disease
VEGF: vascular endothelial growth factor II. Terms Unless otherwise noted, technical terms are used according to conventional usage. Definitions of common terms in molecular biology may be found in Benjamin Lewin, *Genes*

V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Angiogenesis: A biological process leading to the generation of new blood vessels through sprouting or growth from pre-existing blood vessels. The process involves the migration and proliferation of endothelial cells from preexisting vessels. Angiogenesis occurs during pre-natal development, post-natal development, and in the adult. In the adult, angiogenesis occurs during the normal cycle of the female reproductive system, wound healing, and during pathological processes such as cancer (for a review see Battegay, *J. Molec. Med.* 73(7): 333-346, 1995).

Angiogenic Activity: Promotion of angiogenesis. Angiogenic activity can be measured in an angiogenesis assay. For discussion of several angiogenesis assays, see section VII, below.

Angiogenic Factor: A molecule that promotes angiogenesis. Numerous experiments have suggested that tissues secrete factors that promote angiogenesis under conditions of poor blood supply during normal and pathological angiogenesis processes. Angiogenic molecules are generated by tumor, inflammatory, and connective tissue cells in response to hypoxia and other as-yet ill-defined stimuli. Non-limiting examples of angiogenic factors include bFGF, VEGF, and PAMP (demonstrated herein).

The first indication of the existence of diffusible angiogenic substances was gleaned from filtration experiments demonstrating that tumor cells separated from underlying tissues by filters that do not allow passage of cells are nevertheless capable of supporting vessel growth in these tissues. The formation of blood vessels is initiated and maintained by a variety of factors secreted either by the tumor cells themselves or by accessory cells. Many different growth factors and cytokines have been shown to exert chemotactic, mitogenic, modulatory or inhibitory activities on endothelial cells, smooth muscle cell and fibroblasts and can, therefore, be expected to participate in an angiogenic process in one way or another. For example, factors modulating growth, chemotactic behavior and/or functional activities of vascular endothelial cells include aFGF, bFGF, angiogenin, angiotropin, epithelial growth factor, IL-8, and vascular endothelial growth factor (VEGF), among others.

Because many angiogenic factors are mitogenic and chemotactic for endothelial cells, their biological activities (angiogenic activities) can be determined in vitro by measuring the induced migration of endothelial cells or the effect of these factors on endothelial cell proliferation. Alternatively, a bioassay may be utilized for direct determination of angiogenic activities. Such a bioassay permits repeated, long-term quantitation of angiogenesis as well as physiological characterization of angiogenic vessels. Many such assays are known in the art.

One assay employs the use of a non-vascularized mouse eye (for example, see Kenyon et al., *Invest Opthalmol. Vis. Sci.* 37:1625, 1996; also see Examples below) or the rabbit eye (for example, see Gaudric et al. *Ophthal. Res.* 24: 181, 1992), and is termed a cornea pocket assay. This assay has the advantage that new blood vessels are easily detected and essentially must be newly formed blood vessels in the normally avascular cornea.

Another assay involves the use of chicken chorioallantoic membrane (the CAM assay; see Wilting et al., *Anat. Embryol.* 183: 259, 1991). Other assays in the rat, such as the rat aortic ring model, provide reproducible assays that are often utilized to identify angiogenic agonists and antagonists (for example, see Lichtenberg et al., *Pharmacol Toxicol.* 84: 34, 1999).

A third type of angiogenesis assay is termed a Directed in vivo Angiogenesis Assay (DIVAA; Martinez et al., *J. Natl. Cancer Inst.*, 21;94(16):1226-37, 2002; see Example 1).

A fourth assay, termed the embryonic chick aortic ring assay, uses aortic tissue from chicks embedded in collagen. Outgrowth of blood vessels is monitored microscopically. By way of example, see Isaacs, et al., *J. Biol. Chem.*, 16;277(33): 29936-44, 2002; and Martinez et al., *J. Natl. Cancer Inst.*, 21;94(16):1226-37, 2002.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term antibody includes intact immunoglobulins as well as a number of well-characterized fragments produced by digestion with various peptidases, or genetically engineered "artificial" antibodies. Thus, for example, pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region thereby converting the $F(ab)'_2$ dimer into an Fab' monomer. The Fab' monomer is essentially a Fab with part of the hinge region (see, *Fundamental Immunology*, W. E. Paul, ed., Raven Press, N.Y., 1993). While various antibody fragments are defined in terms of the digestion of an intact antibody, it will be appreciated that Fab' fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

Antibodies for use in the methods and devices of this disclosure can be monoclonal or polyclonal. Merely by way of example, monoclonal antibodies can be prepared from murine hybridomas according to the classical method of Kohler and Milstein (*Nature* 256:495-497, 1975) or derivative methods thereof. Detailed procedures for monoclonal antibody production are described in Harlow and Lane (*Antibodies, A Laboratory Manual*, CSHL, New York, 1988).

Administration (of PAMP or a PAMP inhibitor): Administration of PAMP or a PAMP inhibitor can be by any route known to one of skill in the art. Administration can be local or systemic. Examples of local administration include, but are not limited to, topical administration, subcutaneous administration, intramuscular administration, intrathecal administration, intrapericardial administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ or tumor. Thus, in particular embodiments, local administration includes intra-arterial administration and intravenous administration when such administration is targeted to the vasculature supplying a particular organ or tumor.

Systemic administration includes any route of administration designed to distribute PAMP or a PAMP inhibitor widely throughout the body via the circulatory system. Thus, systemic administration includes, but is not limited to, intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In one embodiment, an antigen is a PAMP antigen.

Antisense, Sense, and Antigene: Double-stranded DNA (dsDNA) has two strands, a 5'->3' strand, referred to as the plus strand, and a 3'->5' strand (the reverse compliment), referred to as the minus strand. Because RNA polymerase adds nucleic acids in a 5'->3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or plus strand DNA. Sense molecules are molecules that are specifically hybridizable or specifically complementary to the minus strand of DNA. Antigene molecules are either antisense or sense molecules complimentary to a dsDNA target. In one embodiment, an antisense molecule specifically hybridizes to a target mRNA and inhibits transcription of the target mRNA.

Arthritis: Arthritis is an inflammatory disease that affects the synovial membranes of one or more joints in the body. It is the most common type of joint disease, and it is characterized by the inflammation of the joint. The disease is usually oligoarticular (affects few joints), but may be generalized. The joints commonly involved include the hips, knees, lower lumbar and cervical vertebrae, proximal and distal interphangeal joints of the fingers, first carpometacarpal joints, and first tarsometatarsal joints of the feet.

One type of arthritis is reactive arthritis, which is an acute nonpurulent arthritis secondary to a urinary tract or gastrointestinal infection with a variety of microorganisms, including *Chlamydia trachomatis, Yersinia, Salmonella, Shigella,* and *Campylobacter*. Microbial components are found in the affected joints. The arthritis appears abruptly and tends to involve the knees and ankles, but sometimes involves the wrists, fingers, and/or toes. Untreated, the arthritis lasts for about a year, then generally abates and only rarely is accompanied by ankylosing spondylitis. Despite evidence of disease being triggered by bacterial infection, viable bacteria are rarely present in affected joints and antibiotic treatment seldom provides relief.

Another type of arthritis is rheumatoid arthritis. Rheumatoid arthritis is a chronic, systemic, inflammatory disease that affects the synovial membranes of multiple joints in the body. Because the disease is systemic, there are many extra-articular features of the disease as well. For example, neuropathy, scleritis, lymphadenopathy, pericarditis, splenomegaly, arteritis, and rheumatoid nodules are frequent components of the disease. In most cases of rheumatoid arthritis, the subject has remissions and exacerbations of the symptoms. Rheumatoid arthritis considered an autoimmune disease that is acquired and in which genetic factors appear to play a role.

Inhibition of angiogenic factors, for example, inhibition of PAMP, can be used to treat arthritis.

Basic Fibroblast Growth Factor (bFGF): A potent mitogen that is widely distributed in many tissue types. Basic FGF is a growth factor, and binds to extracellular matrix components, particularly heparin, from which it is released following injury. Basic FGF is a potent angiogenic factor; the factor first described as "angiogenic growth factor" was later determined to be bFGF.

Cerebral ischemia or ischemic stroke: A condition that occurs when an artery to the brain is partially or completely blocked such that the oxygen demand of the tissue exceeds the oxygen supplied. Deprived of oxygen and other nutrients following an ischemic stroke, the brain suffers damage as a result of the stroke.

Ischemic stroke can be caused by several different kinds of diseases. The most common problem is narrowing of the arteries in the neck or head. This is most often caused by atherosclerosis, or gradual cholesterol deposition. If the arteries become too narrow, blood cells may collect in them and form blood clots (thrombi). These blood clots can block the artery where they are formed (thrombosis), or can dislodge and become trapped in arteries closer to the brain (embolism).

Another cause of stroke is blood clots in the heart, which can occur as a result of irregular heartbeat (for example, atrial fibrillation), heart attack, or abnormalities of the heart valves. While these are the most common causes of ischemic stroke, there are many other possible causes. Examples include use of street drugs, traumatic injury to the blood vessels of the neck, or disorders of blood clotting.

Ischemic stroke is by far the most common kind of stroke, accounting for about 80% of all strokes. Stroke can affect people of all ages, including children. Many people with ischemic strokes are older (60 or more years old), and the risk of stroke increases with older ages. At each age, stroke is more common in men than women, and it is more common among African-Americans than white Americans. Many people with stroke have other problems or conditions which put them at higher risk for stroke, such as high blood pressure (hypertension), heart disease, smoking, or diabetes. Subjects with cerebral ischemia can benefit from angiogenic therapy.

Coronary Artery Disease: In coronary artery disease, the coronary arteries become narrowed (stenosed) or blocked (occluded) by a gradual build-up of fat (cholesterol) within or on the artery wall, which reduces blood flow to the heart muscle. This build-up is called "atherosclerotic plaque" or simply "plaque."

If plaque narrows the lumen or channel of the artery, it may make it difficult for adequate quantities of blood to flow to the heart muscle. If the build-up reduces flow only mildly, there may be no noticeable symptoms at rest, but symptoms such as chest pressure may occur with increased activity or stress. Other symptoms include heartburn, nausea, vomiting, shortness of breath and heavy sweating.

When flow is significantly reduced and the heart muscle does not receive enough blood flow to meet its needs (cardiac ischemia), severe symptoms such as chest pain (angina pectoris), heart attack (myocardial infarction), or rhythm disturbances (arrhythmias) may occur. A heart attack usually is the result of a completely blocked artery, which may damage the heart muscle.

There are three conventional ways to treat atherosclerotic disease: medication, surgery, and minimally invasive interventional procedures such as stent implantation, percutaneous transluminal coronary angioplasty (PTCA), intravascular radiotherapy, atherectomy and excimer laser. The purpose of these treatments is to eliminate or reduce symptoms, and in the case of coronary artery disease decrease the risk of heart attack.

In the case of coronary artery disease, coronary artery bypass graft surgery (CABG), sometimes called "bypass surgery," is a way of creating new channels to carry blood around the blocked areas in the coronary arteries. Also, a surgical intervention called tansyocardial revascularization utilizes a laser that cuts a series of channels in the heart muscle to increase blood flow.

Another type of treatment involves injection of angiogenic factor into the heart in order to induce new blood vessel growth (Henry et al., *JACC* 33 (2:supp A): 384A, 1999). Angiogenic factors (such as bFGF, VEGF, and, as described herein, PAMP) are injected via intraarterial injection, intracoronary injection, or intrapericardial injection.

Endometriosis: A disease affecting women in their reproductive years, in which tissue like the endometrium is found outside the uterus, in other areas of the body. In these locations outside the uterus, the endometrial tissue develops into what are called nodules, lesions, implants, or growths. These growths can cause pain, infertility, and other problems.

The most common locations of endometrial growths are in the abdomen, including the ligaments supporting the uterus, the area between the vagina and the rectum, the outer surface of the uterus, and the lining of the pelvic cavity. Sometimes the growths are also found in abdominal surgery scars, on the intestines or in the rectum or on the bladder, vagina, cervix, or vulva (external genitals). Endometrial growths have also been found outside the abdomen, in the lung, arm, thigh and other locations, but these are uncommon.

Endometrial growths are generally not malignant or cancerous, however, in recent decades there has been an increased frequency of malignancy occurring or being recognized in conjunction with endometriosis. Like the lining of the uterus, endometrial growths usually respond to the hormones of the menstrual cycle. They build up tissue each month, break down, and cause bleeding. However, unlike the lining of the uterus, endometrial tissue outside the uterus has no way of leaving the body. The result is internal bleeding, degeneration of the blood and tissue shed from the growths, inflammation of the surrounding areas, and formation of scar tissue. Other complications, depending on the location of the growths, can be rupture of growths (which can spread endometriosis to new areas), the formation of adhesions, intestinal bleeding or obstruction (if the growths are in or near the intestines), interference with bladder function (if the growths are on or in the bladder), and other problems. Symptoms seem to worsen with time, though cycles of remission and reoccurrence are the pattern in some cases.

The most common symptoms of endometriosis are pain before and during menstrual periods, during or after sexual activity, infertility, and heavy or irregular bleeding. Other symptoms may include fatigue, painful bowel movements with menstrual periods, lower back pain with periods, diarrhea, and constipation and other intestinal upset. Some women with endometriosis have no symptoms. Infertility affects about 30-40% of women with endometriosis and is a common result with progression of the disease.

As described herein, inhibition of angiogenic factors, for example, inhibition of PAMP, can be used to treat endometriosis.

Epitope: An antigenic determinant. These are particular chemical groups or peptide sequences on a molecule that are antigenic, for instance, that elicit a specific immune response. An antibody binds a particular antigenic epitope, based on a 3-D structure of the antibody and the matching or cognate epitope.

Functionally equivalent sequence variant: Sequence alterations, for example in PAMP or in peptide inhibitors of PAMP, that yield the same results as described herein. Such sequence alterations can include, but are not limited to, deletions, base modifications, mutations, labeling, and insertions.

Function-blocking or function-neutralizing antibody: An antibody capable of inhibiting, to some measurable extent, the angiogenic activity of PAMP.

Fusion protein: A protein comprising two amino acid sequences that are not found joined together in nature. PAMP fusion proteins specifically comprise at least (1) the amino acid sequence shown in SEQ ID NO: 4 or a sequence sharing 90% or 95% sequence identity with SEQ ID NO: 4, and (2) a peptide portion placed at either end of or within the amino acid sequence shown in SEQ ID NO: 4 or sequence sharing 90% or 95% sequence identity with SEQ ID NO: 4. Such PAMP fusion proteins can additionally include other protein elements, such as a linker between such peptide portions.

Graft: Material, especially living tissue or an organ, surgically attached to or inserted into a bodily part to replace a damaged part or compensate for a defect Particular examples of grafts include organ grafts and skin grafts.

Inhibitor (for example, of an angiogenic activity of PAMP): A substance capable of inhibiting, to some measurable extent, an activity (such as a biological activity) of a specific molecule.

In particular described embodiments, the inhibitor is an inhibitor of angiogenic activity of PAMP. In some embodiments, an inhibitor is a protein, a peptide, or a fragment, mimetic, analog or derivative thereof, an antisense oligonucleotide, a small inhibitory RNA, or a small molecule inhibitor. In other embodiments, an inhibitor is an antibody. By way of example, in one embodiment, a PAMP inhibitor is a function-neutralizing polyclonal (or monoclonal) PAMP antibody. In another embodiment, a PAMP inhibitor is the peptide PAMP(12-20), which comprises only amino acids 12-20 of PAMP.

A PAMP inhibitor is an agent capable of blocking some portion of PAMP's angiogenic activity. However, in certain embodiments an inhibitor can block at least about 20% of PAMP angiogenic activity. In other embodiments, an inhibitor can block at least about 30%, about 50%, about 60%, about 70%, or about 80% of PAMP angiogenic activity. Under some circumstances, an inhibitor can inhibit an even greater proportion of angiogenic activity of PAMP, and may inhibit at least about 90%, 95%, or even 98% or 100% of PAMP's angiogenic activity. Such particularly high levels of binding inhibition are not required in all circumstances, however.

Inhibition of a PAMP angiogenic activity can be measured using assays known to those of skill in the art. One assay employs the use of a non-vascularized mouse eye (for example, see Kenyon et al., *Invest Opthalmol. Vis. Sci.* 37:1625, 1996; also see Examples below) or the rabbit eye (for example, see Gaudric et al. *Ophthal. Res.* 24: 181, 1992), and is termed a cornea pocket assay. This assay has the advantage that new blood vessels are easily detected and essentially must be newly formed blood vessels in the normally avascular cornea.

Another assay involves the use of chicken chorioallantoic membrane (the CAM assay; see Wilting et al, *Anat. Embryol.* 183: 259, 1991). Other assays in the rat, such as the rat aortic ring model, provide reproducible assays that are often utilized to identify angiogenic agonists and antagonists (for example, see Lichtenberg et al., *Pharmacol Toxicol.* 84: 34, 1999).

A third type of angiogenesis assay is termed a Directed in vivo Angiogenesis Assay (DIVAA; Martinez et al., *J. Natl. Cancer Inst.*, 21;94(16):1226-37, 2002; see Example 1).

A fourth assay, termed the embryonic chick aortic ring assay, uses aortic tissue from chicks embedded in collagen. Outgrowth of blood vessels is monitored microscopically. (for example, see Isaacs, et al., *J. Biol. Chem.*, 16;277(33): 29936-44, 2002; Martinez et al., *J. Natl. Cancer Inst.*, 21;94 (16):1226-37, 2002).

Isolated: An "isolated" biological component (such as a nucleic acid, peptide or protein) has been substantially separated produced apart from, or purified away from other biological components in the cell of the organism in which the component naturally occurs, for instance, other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a host cell as well as chemically synthesized nucleic acids. The term "isolated" or "purified" does not require absolute purity; rather, it is intended as a relative term Thus, for example, an isolated peptide preparation is one in which the peptide or protein is more enriched than the peptide or protein is in its natural environment within a cell. Preferably, a preparation is purified such that the protein or peptide represents at least 50% of the total peptide or protein content of the preparation.

Mammal: This term includes both human and non-human mammals. Similarly, the term "subject" includes both human and veterinary subjects, for example, humans, non-human primates, mice, rats, dogs, cats, horses, and cows.

Neoplasm or tumor: Any new and abnormal growth; particularly a new growth of tissue in which the growth is uncontrolled and progressive. A neoplasm, or tumor, serves no useful function and grows at the expense of the healthy organism.

In general, tumors appear to be caused by abnormal regulation of cell growth. Typically, the growth of cells in the body is strictly controlled; new cells are created to replace older ones or to perform new functions. If the balance of cell growth and death and death is disturbed, a tumor may form. Abnormalities of the immune system, which usually detects and blocks aberrant growth, also can lead to tumors. Other causes include radiation, genetic abnormalities, certain viruses, sunlight, tobacco, benzene, certain poisonous mushrooms, and aflatoxins.

Tumors are classified as either benign (slow-growing and usually harmless depending on the location), malignant (fast-growing and likely to spread and damage other organs or systems) or intermediate (a mixture of benign and malignant cells). Some tumors are more common in men or women, some are more common amongst children or elderly people, and some vary with diet, environment and genetic risk factors.

Symptoms of neoplasms depend on the type and location of the tumor. For example, lung tumors can cause coughing, shortness of breath, or chest pain, while tumors of the colon can cause weight loss, diarrhea, constipation and blood in the stool. Some tumors produce no symptoms, but symptoms that often accompany tumors include fevers, chills, night sweats, weight loss, loss of appetite, fatigue, and malaise.

Blood vessels supply tumors with nutrients and oxygen. Tumor growth is dependent on the generation of new blood vessels that can maintain the needs of the growing tumor, and many tumors secrete substances (angiogenic factors) that are able to induce proliferation of new blood vessels (angiogenesis). As described herein, inhibition of these angiogenic factors, for example, inhibition of PAMP, can reduce angiogenesis and slow or stop tumor growth.

Neovascularization: The growth of new blood vessels. Neovascularization can be the proliferation of blood vessels in tissue not normally containing them, or the proliferation of blood vessels in an ischemic or otherwise damaged tissue. Neovascularization can be pathological, for example when it occurs in the retina or cornea.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide or "oligo": Multiple nucleotides (for instance, molecules comprising a sugar (for example, ribose or deoxyribose) linked to a phosphate group and to an exchangeable organic base, which is either a substituted pyrimidine (Py) (for example, cytosine (C), thymine (T) or uracil (U)) or a substituted purine (Pu) (for example, adenine (A) or guanine (G)). The term "oligonucleotide" as used herein refers to both oligoribonucleotides (ORNs) and oligodeoxyribonucleotides (ODNs). The term "oligonucleotide" also includes oligonucleosides (for instance, an oligonucleotide minus the phosphate) and any other organic base polymer. Oligonucleotides can be obtained from existing nucleic acid sources (for example, genomic or cDNA), but can also be synthetic (for example, produced by laboratory or in vitro oligonucleotide synthesis).

PAMP: See proadrenomedullin N-terminal 20 peptide.

Peripheral Vascular Disease (PVD): A condition in which the arteries that carry blood to the arms or legs become narrowed or occluded. This interferes with the normal flow of blood, sometimes causing pain but often causing no readily detectable symptoms at all.

The most common cause of PVD is atherosclerosis, a gradual process in which cholesterol and scar tissue build up, forming plaques that occlude the blood vessels. In some cases, PVD may be caused by blood clots that lodge in the arteries and restrict blood flow.

PVD affects about one in 20 people over the age of 50, or 8 million people in the United States. More than half the people with PVD experience leg pain, numbness or other symptoms, but many people dismiss these signs as "a normal part of aging" and do not seek medical help.

The most common symptom of PVD is painful cramping in the leg or hip, particularly when walking. This symptom, also known as "claudication," occurs when there is not enough blood flowing to the leg muscles during exercise, such that ischemia occurs. The pain typically goes away when the muscles are rested.

Other symptoms may include numbness, tingling or weakness in the leg. In severe cases, people with PVD may experience a burning or aching pain in an extremity such as the foot or toes while resting, or may develop a sore on the leg or foot that does not heal. People with PVD also may experience a cooling or color change in the skin of the legs or feet, or loss of hair on the legs. In extreme cases, untreated PVD can lead to gangrene, a serious condition that may require amputation of a leg, foot or toes. People with PVD are also at higher risk for heart disease and stroke.

As described herein, people with PVD can benefit from treatment with angiogenic agents, such as PAMP.

Pharmaceutical agent or drug: A chemical compound or composition capable of inducing a desired therapeutic or prophylactic effect when properly administered to a subject. Pharmaceutical agents include, but are not limited to, angiogenic factors, for example PAMP, bFGF, and VFGF, and anti-angiogenic factors, such as inhibitors of PAMP, bFGF, or VEGF. For example, suitable anti-angiogenic factors include, but are not limited to, SU5416, which is a specific VEGF-R antagonist, and SU6668 which blocks the receptors for VEGF, bFGF, and PDGF. See, for example, Liu et al, *Seminars in Oncology* 29 (Suppl 11): 96-103, 2002; Shepherd et al., *Lung Cancer* 34:S81-S89, 2001.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the peptides herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or treating a disease: "Preventing" a disease refers to inhibiting the full development of a disease, for example inhibiting the development of myocardial infarction in a person who has coronary artery disease or inhibiting the progression or metastasis of a tumor in a subject with a neoplasm "Treatment" refers to a therapeutic intervention that ameliorates a sign or symptom of a disease or pathological condition after it has begun to develop.

Proadrenomedullin N-terminal 20 peptide (PAMP): A 20 amino-acid molecule originating from the post-translational processing of pre-proadrenomedullin (see, for example, Ishimitsu et al., *Biochem. Biophys. Res. Commun.* 203, 631-639, 1994). As described herein, the term PAMP includes the PAMP amino acid sequence shown in SEQ ID NO: 4, variant PAMP amino acid sequences that share 90% or 95% sequence identity with SEQ ID NO: 4 and retain angiogenic activity, PAMP fragments that retain angiogenic activity, and PAMP fusion proteins that retain angiogenic activity. Angiogenic activity can be assessed using any of the angiogenesis assays described herein. As defined herein, a variant PAMP sequence, PAMP fragment, or PAMP fusion protein retains angiogenic activity if it retains at least a portion of the angiogenic activity of PAMP, for example 25%, 50%, 75%, 90%, or 95% of the angiogenic activity of PAMP, as measured in an angiogenesis assay, for example the DIVAA assay described herein.

PAMP has been detected in several different mammalian tissues, including brain, pituitary gland, and adrenal glands, and is a potent hypotensive and vasodilatory agent (see, for example, Kitamura et al., *FEBS Lett.* 351, 35-37, 1994; Saita et al., *Regul. Pept.* 77(1-3):147-153, 1998). Numerous activities have been attributed to PAMP, most related to the physiologic control of fluid and electrolyte homeostasis. For example, PAMP inhibits aldosterone secretion by acting directly on the adrenal glands. In the pituitary gland, the peptide inhibits basal adrenocorticotropic hormone (ACTH) secretion. In general, PAMP appears to act in brain and pituitary gland to facilitate the loss of plasma volume, actions which complement its vasodilatory effects in blood vessels.

As described herein, in addition to its hypotensive and vasodilatory effects, PAMP functions as a potent angiogenic factor. When compared to other well-known angiogenic factors, such as vascular endothelial growth factor (VEGF) and basic fibroblast growth factor (bFGF), PAMP is roughly one million times more potent, based on testing in the embryonic chick aortic ring assay, and Directed in vivo Angiogenesis Assay (DIVAA).

Psoriasis: A chronic skin disease characterized by scaling and inflammation. Scaling occurs when cells in the outer layer of the skin reproduce faster than normal and pile up on the skin's surface.

Psoriasis affects between one and two percent of the United States population, or about 5.5 million people. Although the disease occurs in all age groups and about equally in men and women, it primarily affects adults. People with psoriasis may suffer discomfort, including pain and itching, restricted motion in their joints, and emotional distress.

In its most typical form, psoriasis results in patches of thick, red skin covered with silvery scales. These patches, which are sometimes referred to as plaques, usually itch and may burn. The skin at the joints may crack. Psoriasis most often occurs on the elbows, knees, scalp, lower back, face, palms, and soles of the feet, but it can affect any skin site. The disease may also affect the fingernails, the toenails, and the soft tissues inside the mouth and at the genitalia.

Histologic studies, including electron microscopy, have clearly established that alterations in the blood vessel formation in the skin are a prominent feature of psoriasis. Thus, as described herein, subjects with psoriasis can benefit from anti-angiogenic therapy, such as treatment with PAMP inhibitors.

Retinopathy: Retinopathy is an eye disease affecting the blood vessels in the retina, for example, in a person with diabetes. Over time, diabetes affects the circulatory system of the retina. The earliest phase of the disease is known as background diabetic retinopathy. In this phase, the arteries in the retina become weakened and leak, forming small, dothike hemorrhages. These leaking vessels often lead to swelling or edema in the retina and decreased vision.

The next stage is known as proliferative diabetic retinopathy. In this stage, circulation problems cause areas of the retina to become oxygen-deprived or ischemic. New, fragile, vessels develop as the circulatory system attempts to maintain adequate oxygen levels within the retina. This is called neovascularization. Unfortunately, these delicate vessels hemorrhage easily. Blood may leak into the retina and vitreous, causing spots or floaters, along with decreased vision.

In the later phases of the disease, continued abnormal vessel growth and scar tissue may cause serious problems, such as retinal detachment and glaucoma.

As described herein, subjects with retinopathy can benefit from anti-angiogenesis therapy, such as treatment with PAMP inhibitors.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.* 2: 482, 1981); Needleman and Wunsch (*J. Mol. Biol.* 48: 443, 1970); Pearson and Lipman (*PNAS. USA* 85: 2444, 1988); Higgins and Sharp (*Gene*, 73: 237-244, 1988); Higgins and Sharp (*CABIOS* 5: 151-153, 1989); Corpet et al. (*Nuc. Acids Res.* 16: 10881-10890, 1988); Huang et al. (*Comp. Appls Biosci.* 8: 155-165, 1992); and Pearson et al. (*Meth. Mol. Biol.* 24: 307-31, 1994). Altschul et al. (*Nature Genet.*, 6: 119-129, 1994) presents a detailed consideration of sequence alignment methods and homology calculations.

The alignment tools ALIGN (Myers and Miller, *CABIOS* 4:11-17, 1989) or LFASTA (Pearson and Lipman, 1988) may be used to perform sequence comparisons (Internet Program© 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at the NCSA Website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.* 215:403-410, 1990; Gish & States, *Nature Genet.* 3:266-272, 1993; Madden et al. *Meth. Enzymol.* 266:131-141, 1996; Altschnul et al., *Nucleic Acids Res.* 25:3389-3402, 1997; and Zhang & Madden, *Genome Res.* 7:649-656, 1997.

Orthologs of proteins are typically characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of one or both binding domains of the disclosed peptides.

When significantly less than the entire sequence is being compared for sequence identity, homologous sequences will typically possess at least 80% sequence identity over short windows of 10-20 amino acids, and may possess sequence identities of at least 85%, at least 90%, at least 95%, or at least 99% depending on their similarity to the reference sequence. Sequence identity over such short windows can be determined using LFASTA; methods are described at the NCSA Website. One of skill in the art will appreciate that these sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Conditions for nucleic acid hybridization and calculation of stringencies can be found in Sambrook et al. (In *Molecular Cloning: A Laboratory Manual*, Cold Spring Harbor, N.Y., 1989) and Tijssen (*Laboratory Techniques in Biochemistry and Molecular Biology Part I, Ch.* 2, Elsevier, N.Y., 1993). Nucleic acid molecules that hybridize under stringent conditions to the disclosed peptide sequences will typically hybridize to a probe based on either the entire peptide encoding sequence, an entire binding domain, or other selected portions of the encoding sequence under wash conditions of 0.2×SSC, 0.1% SDS at 65° C.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Small molecule inhibitor (for example, of an angiogenic activity of PAMP): A molecule, typically with a molecular weight less than 1000, or in some embodiments, less than about 500 Daltons, wherein the molecule is capable of inhibiting, to some measurable extent, an activity of some target molecule. In particular embodiments, the small molecule inhibitor is an inhibitor of an angiogenic activity of PAMP.

Therapeutically effective dose: A dose sufficient to prevent advancements or to cause regression of the disease, or which is capable of relieving symptoms caused by the disease, such as angina or limb pain. For example, a therapeutically effective amount of PAMP or PAMP inhibitor can vary from about 0.1 nM per kilogram (kg) body weight to about 1 µM per kg body weight, such as about 1 nM to about 500 nM per kg body weight, or about 5 nM to about 50 nM per kg body weight The exact dose is readily determined by one of skill in the art based on the potency of the specific compound, the age, weight, sex and physiological condition of the subject.

Variants or fragments of Proadrenomedullin N-terminal 20 peptide (PAMP): A peptide that shares at least 90% sequence identity with SEQ ID NO: 4 and that retains angiogenic activity, for example, 25%, 50%, 75%, or even 100% of the angiogenic activity of PAMP. For more discussion of variants and fragments, see section VI, below. For a discussion of various assays that can be used to measure angiogenic activity, see section VII, below.

Vascular Endothelial Growth Factor (VEGF): VEGF is a homodimeric heavily glycosylated protein of 46-48 kDa (24 kDa subunits). Glycosylation is not required, however, for biological activity. The subunits are linked by disulphide bonds.

VEGF is a highly specific mitogen for vascular endothelial cells. In vitro, the two shorter forms of VEGF stimulate the proliferation of macrovascular endothelial cells. VEGF does not appear to enhance the proliferation of other cell types. VEGF significantly influences vascular permeability and is a strong angiogenic protein in several bioassays. VEGF also probably plays a role in neo-vascularisation under physiological conditions. A potent synergism between VEGF and bFGF in the induction of angiogenesis has been observed. It has been suggested that VEGF released from smooth muscle cells and macrophages may play a role in the development of arteriosclerotic diseases.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Description of Several Embodiments

A first embodiment is a method of inducing angiogenesis in a tissue. The method includes introducing into the tissue an effective amount of the peptide shown in SEQ ID NO: 4 or a variant or fragment thereof that has at least 90% sequence identity with SEQ ID NO: 4 and that retains angiogenic activity, thereby inducing angiogenesis in the tissue. In some examples of the method, the variant or fragment has at least 95% sequence identity with SEQ ID NO: 4, whereas in other examples, the peptide is the peptide shown in SEQ ID NO: 4. In some examples of the method, the tissue is a graft, heart tissue, a blood vessel, a wound, or a coronary artery. In particular examples, the graft is a skin or organ graft.

In some examples of the method introducing includes local administration to an affected area, for example topical administration, intra-arterial administration, or intravenous administration to peripheral vessels that perfuse a target, subcutaneous administration, intramuscular administration, intrathecal administration, intrapericardial administration, intra-ocular administration, topical ophthalmic administration, or administration to nasal mucosa or lungs by inhalation. In other examples, introducing includes systemic administration, for example by intra-arterial, intravenous, or other parenteral routes for generalized systemic distribution throughout the body. In particular examples, inducing angiogenesis includes inducing neovascularization.

Another embodiment is a method of promoting angiogenesis in a target area in a subject where angiogenesis is desired. The method includes introducing into the target area a therapeutically effective amount of the peptide shown as SEQ ID NO: 4 or a variant or fragment thereof that has at least 90% sequence identity with SEQ ID NO: 4 and that retains angiogenic activity, thereby promoting angiogenesis in the target area in the subject. In some examples of the method, the variant or fragment has at least 95% sequence identity with SEQ ID NO: 4, whereas in other examples, the peptide is the peptide shown in SEQ ID NO: 4. In some examples of the method, the tissue is a tissue graft, heart tissue, a blood vessel a wound, or a coronary artery. In particular examples, the graft is a skin or organ graft, or a surgical reattachment of an extremity, such as a finger, hand, or arm.

In certain examples, the subject has or is at risk for developing coronary artery disease, peripheral vascular disease, cerebral ischemia, or a wound. In particular examples of the method, the area is a vessel in which blood flow is restricted, and/or normally perfused tissue is rendered ischemic.

Further embodiments are the peptide of SEQ ID NO: 4 or a variant or fragment thereof that has at least 90% or 95% sequence identity with SEQ ID NO: 4 and that retains angiogenic activity, for use in a pharmaceutical composition for inducing angiogenesis. In some embodiments, the peptide is SEQ ID NO: 4, and in other embodiments, the use is for promoting revascularization to treat coronary artery disease, peripheral vascular disease, or to promote revascularization and healing of a wound. Encouraging revascularization is particularly important for slow healing or non-healing wounds, for example, skin lesions in subjects with peripheral vascular disease, or decubital ulcers in bedridden subjects.

Also disclosed is a kit for inducing angiogenesis in a tissue in a subject, comprising a container and an amount of SEQ ID NO: 4 or a variant or fragment thereof that has at least 90% sequence identity with SEQ ID NO: 4 and that retains angiogenic activity. In some examples, the kit includes a container comprising a second angiogenic agent In certain examples, the second angiogenic agent is vascular endothelial growth factor or basic fibroblast growth factor, and in particular examples, the kit also includes instructions for administering the peptide to a subject.

Also disclosed herein is a method of inhibiting angiogenesis in a tissue wherein the formation of new blood vessels is not desired, thereby inhibiting pathological neovascularization. The method includes introducing into the tissue an effective amount of an inhibitor of proadrenomedullin N-terminal 20 peptide (PAMP), thereby inhibiting angiogenesis in the tissue. In some examples, the inhibitor is an antibody, a small molecule inhibitor; or an antisense oligonucleotide. In certain examples, the inhibitor is proadrenomedullin N-terminal 20 peptide (12-20). In some embodiments of the method, the tissue includes a neoplasm, a retina, or a cornea.

Further embodiments are methods of inhibiting angiogenesis in a target area in a subject where the inhibition of angiogenesis is desired. The method includes introducing into the target area a therapeutically effective amount of a proadrenomedullin N-terminal 20 peptide (PAMP) inhibitor, thereby inhibiting angiogenesis in the subject. In some examples, the inhibitor is an antibody, a small molecule inhibitor, or an antisense oligonucleotide. In certain examples, the inhibitor is proadrenomedullin N-terminal 20 peptide (12-20).

In some embodiments of the method, the issue includes skin, a tumor, a retina, a joint, or endometrial tissue. In particular examples, the subject has or is at risk for developing a tumor, retinopathy, endometriosis, arthritis, or psoriasis. In some examples of the method introducing includes local administration, for example topical administration, intra-arterial administration, intravenous administration, subcutaneous administration, intramuscular administration, intrathecal administration, intrapericardial administration, intra-ocular administration, topical ophthalmic administration, or administration by inhalation. In other examples, introducing includes systemic administration.

Further embodiments are proadrenomedullin N-terminal 20 peptide (12-20) for use in a pharmaceutical composition for inhibiting angiogenesis. In particular examples, use is for treating a tumor, retinopathy, endometriosis, arthritis, or psoriasis.

Also disclosed herein is a kit for inhibiting angiogenesis in a tissue in a subject. The kit includes a container and an amount of proadrenomedullin N-terminal 20 peptide (12-20). In some examples, the container contains an additional anti-angiogenic agent, for example, an inhibitor of vascular endothelial growth factor (VEGF) or an inhibitor of basic fibroblast growth factor (bFGF). In certain examples, the kit also includes instructions for administering the peptide to a subject.

Still further embodiments are methods of screening for an inhibitor of proadrenomedullin N-terminal 20 peptide (PAMP). The method includes screening a library of small molecules for disruption of the binding of anti-PAMP antibody to PAMP, and screening a molecule identified as disrupting the binding of anti-PAMP antibody to PAMP for anti-angiogenesis activity in an angiogenesis bioassay.

IV. PAMP and PAMP Inhibitors

Proadrenomedullin N-terminal 20 peptide (PAMP) is a 20 amino-acid peptide molecule originating from the post-translational processing of pre-proadrenomedullin (see, for example, Ishimitsu et al., *Biochem. Biophys. Res. Commun.* 203, 631-639, 1994). PAMP has been detected in numerous different mammalian issues, including brain, pituitary gland, and adrenal glands.

PAMP is known for its potent hypotensive and vasodilatory effects (see, for example, Kitamura et al., *FEBS Lett.* 351, 35-37, 1994; Saita et al., *Regul. Pept.* 77(1-3):147-153, 1998). Numerous activities have been attributed to PAMP, most related to the physiologic control of fluid and electrolyte homeostasis. For example, PAMP inhibits aldosterone secretion by acting directly on the adrenal glands. In the pituitary gland, the peptide inhibits basal adrenocorticotropic hormone (ACTH) secretion. In general PAMP appears to act in brain and pituitary gland to facilitate the loss of plasma volume, actions which complement its vasodilatory effects in blood vessels.

In addition to its hypotensive and vasodilatory effects, it is now shown herein that PAMP functions as a potent angiogenic factor. When compared to other well-known angiogenic factors, such as vascular endothelial growth factor (VEGF) and basic fibroblast growth factor (bFGF), PAMP is roughly one million times more potent.

PAMP can be used to promote angiogenesis, for example in subjects with coronary artery disease, peripheral vascular disease, or cerebral ischemia.

Inhibitors of PAMP are also useful for inhibiting angiogenesis in vivo. For example, PAMP inhibitors can be used to inhibit the growth of tumors. Tumor growth is dependent on the generation of new blood vessels that maintain the growing needs of the tumor. Thus, treatment of these tumors with PAMP inhibitors to cuts off blood supply to the tumors, effectively starving them and inhibiting tumor growth. PAMP inhibitors are also of use in treating other diseases characterized by excessive angiogenesis, such as psoriasis, diabetic retinopathy, and endometriosis.

V. Production of PAMP Antibodies

Optimally, antibodies raised against PAMP would specifically detect that peptide or inhibit the angiogenic activity of PAMP. Antibodies that specifically detect PAMP would recognize and bind the PAMP peptide and would not substantially recognize or bind to other proteins or peptides found in a biological sample. The determination that an antibody specifically detects its target protein is made by any one of a number of standard immunoassay methods; for instance, the Western blotting technique (Sambrook et al., In *Molecular Cloning: A Laboratory Manual*, CSHL, New York, 1989).

To determine by Western blotting that a given antibody preparation (such as one produced in a mouse or rabbit) specifically detects the target peptide, the peptide of interest is synthesized and transferred to a membrane (for example, nitrocellulose) by Western blotting, and the test antibody preparation is incubated with the membrane. After washing the membrane to remove non-specifically bound antibodies, the presence of specifically bound antibodies is detected by the use of an anti-mouse or anti-rabbit antibody conjugated to an enzyme such as alkaline phosphatase.

Application of an alkaline phosphatase substrate 5-bromo-4-chloro-3-indolyl phosphate/nitro blue tetrazolium results in the production of a dense blue compound by immnnolocalized alkaline phosphatase. Antibodies that specifically detect the target PAMP peptide will, by this technique, be shown to bind to the target PAMP peptide band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-PAMP peptide binding.

The determination that an antibody inhibits the angiogenic activity of PAMP may be made, for example, using an angiogenesis assay, for instance any of the angiogenesis assays described herein (see section VII, below). For instance, the determination that an antibody inhibits the angiogenic activity of PAMP can be made by comparing the angiogenic activity of PAMP alone with the angiogenic activity of PAMP in the presence of the PAMP antibody using the DIVAA assay. An antibody that inhibits the angiogenic activity of PAMP will reduce the angiogenic activity of PAMP in the DIVAA assay by a certain amount, for example, by 20%, 30%, 40%, 50%, 60%, 70%, 80%, 90%, or even by 100%.

A. Monoclonal Antibody Production by Hybridoma Fusion

Monoclonal antibody to epitopes of PAMP peptide can be prepared from murine hybridomas according to the classical method of Kohler and Milstein (*Nature* 256:495, 1975) or derivative methods thereof. Briefly, a mouse is repetitively inoculated with a few micrograms of the selected protein over a period of a few weeks. The mouse is then sacrificed, and the antibody-producing cells of the spleen are isolated. The spleen cells are fused by means of polyethylene glycol with mouse myeloma cells, and the excess un-fused cells destroyed by growth of the system on selective media comprising amid (HAT media). The successfully fused cells are diluted and aliquots of the dilution placed in wells of a microtiter plate where growth of the culture is continued. Antibody-producing clones are identified by detection of antibody in the supeunatant fluid of the wells by immunoassay procedures, such as ELISA, as originally described by Engvall (*Enzymol.* 70:419, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

B. Polyclonal Antibody Production by Immunization

Polyclonal antiserum containing antibodies to heterogeneous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.* 33:988-991, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In *Handbook of Experimental Inmmunology*, Wier, D. (ed.) chapter 19. Blackwell, 1973). Plateau concentration of antibody is usually in the range of about 0.1 to 0.2 mg/ml of serum (about 12 µM. Affinity of the antisera for the antigen is determined by preparing competitive binding curves, as described, for example, by Fisher (*Manual of Clinical Immunology*, Ch. 42, 1980).

C. Antibodies Raised Against Synthetic Peptides

A third approach to raising antibodies against PAMP peptide is to use synthetic peptides synthesized on a commercially available peptide synthesizer based upon the amino acid sequence of PAMP.

By way of example only, polyclonal antibodies to PAMP peptide can be generated through well-known techniques by injecting rabbits with chemically synthesized peptide.

D. Antibodies Raised by Injection of a PAMP Peptide-Encoding Sequence

Antibodies may be raised against PAMP peptide by subcutaneous injection of a DNA vector that expresses PAMP peptide into laboratory animals, such as mice. Delivery of the recombinant vector into the animals may be achieved using a hand-held form of the Biolistic system (Sanford et al., *Particulate Sci. Technol.* 5:27-37, 1987) as described by Tang et al. (*Nature* 356:152-154, 1992). Expression vectors suitable for this purpose may include those that express the PAMP peptide-encoding sequence under the transcriptional control of either the human β-actin promoter or the cytomegalovirus (CMV) promoter.

VI. Variation of PAMP and PAMP Inhibitor Peptides

A. Sequence Variants

The angiogenic or anti-angiogenic characteristics of the peptides disclosed herein lie not in the precise amino acid sequence, but rather in the three-dimensional structure inherent in the amino acid sequences encoded by the DNA sequences. It is possible to recreate the binding characteristics of any of these peptides, for instance the binding characteristics of PAMP, by recreating the three-dimensional structure, without necessarily recreating the exact amino acid sequence. This can be achieved by designing a nucleic acid sequence that encodes for the three-dimensional structure, but which differs, for instance by reason of the redundancy of the genetic code. Similarly, the DNA sequence may also be varied, while still producing a functional angiogenic or anti-angiogenic peptide.

Variant angiogenic or anti-angiogenic peptides include peptides that differ in amino acid sequence from the disclosed sequence, but that share structurally significant sequence homology with any of the provided peptides. Such variants may be produced by manipulating the nucleotide sequence of the encoding sequence, using standard procedures, including site-directed mutagenesis or PCR. The simplest modifications involve the substitution of one or more amino acids for amino acids having similar biochemical properties. These so-called conservative substitutions are likely to have minimal impact on the activity of the resultant peptide, especially when made outside of the binding site of the peptide. Table 1 shows amino acids that may be substituted for an original amino acid in a peptide, and which are regarded as conservative substitutions.

TABLE 1

| Orignal Residue | Conservative Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in peptide structure may be obtained by selecting amino acid substitutions that are less conservative than those listed in Table 1. Such changes include changing residues that differ more significantly in their effect on maintaining polypeptide backbone structure (for example, sheet or helical conformation) near the substitution, charge or hydrophobicity of the molecule at the target site, or bulk of a specific side chain. The following substitutions are generally expected to produce the greatest changes in protein properties: (a) a hydrophilic residue (for example, seryl or threonyl) is substituted for (or by) a hydrophobic residue (for example, leucyl isoleucyl, phenylalanyl, valyl or alanyl); (b) a cysteine or proline is substituted for (or by) any other residue; (c) a residue having an electropositive side chain (for example, lysyl, arginyl, or histadyl) is substituted for (or by) an electronegative residue (for example, glutamnyl or aspartyl); or (d) a residue having a bulky side chain (for example, phenylalanine) is substituted for (or by) one lacking a side chain (for example, glycine).

Variant angiogenic or anti-angiogenic-encoding sequences may be produced by standard DNA mutagenesis techniques, for example, M13 primer mutagenesis. Details of these techniques are provided in Sambrook (In *Molecular Cloning: A Laboratory Manual,* Cold Spring Harbor, N.Y. 1989), Ch. 15. By the use of such techniques, variants may be created which differ in minor ways from the angiogenic and anti-angiogenic-encoding sequences disclosed. DNA molecules and nucleotide sequences which are derivatives of those specifically disclosed herein and that differ from those disclosed by the deletion, addition, or substitution of nucleotides while still encoding a peptide that promotes or inhibits angiogenesis, are comprehended by this disclosure. In their most simple form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence such that, while the nucleotide sequence is substantially altered, it nevertheless encodes a peptide having an amino acid sequence substantially similar to the disclosed peptide sequences. For example, the first amino acid residue of PAMP is alanine. The nucleotide codon triplet GCT encodes this alanine residue. Because of the degeneracy of the genetic code, three other nucleotide codon triplets—GCG, GCC and GCA)—also code for alanine. Thus, the nucleotide sequence of the PAMP-encoding sequence could be changed at this position to any of these three alternative codons without affecting the amino acid composition or characteristics of the encoded peptide. Based upon the degeneracy of the genetic code, variant DNA molecules may be derived from the cDNA and gene sequences disclosed herein using standard DNA mutagenesis techniques as described above, or by synthesis of DNA sequences. Thus, this disclosure also encompasses nucleic acid sequences which encode PAMP, but which vary from the disclosed nucleic acid sequences by virtue of the degeneracy of the genetic code.

B. Peptide Modifications

The present disclosure includes biologically active molecules that mimic the action of the PAMP and PAMP inhibitor peptides of the present disclosure. The peptides of the disclosure include synthetic embodiments of naturally-occurring peptides described herein, as well as analogues (non-peptide organic molecules), derivatives (chemically functionalized protein molecules obtained starting with the disclosed peptide sequences) and variants (homologs) of these peptides that specifically bind with PAMP receptors. Each peptide of the disclosure is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the peptides, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptides, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability.

Peptidomimetic and organomimetic embodiments are also within the scope of the present disclosure, whereby the three-dimensional arrangement of the chemical constituents of such peptido- and organomimetics mimic the three dimensional arrangement of the peptide backbone and component amino acid side chains in the PAMP or PAMP inhibitor peptides, resulting in such peptido- and organomimetics of the peptides of this disclosure having measurable or enhanced angiogenic or anti-angiogenic activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology,* Interpharm Press: Buffalo Grove, Ill., pp. 165-174 and *Principles of Pharmacology Munson* (ed.) 1995, Ch. 102, for descriptions of techniques used in CADD. Also included within the scope of the disclosure are mimetics prepared using such techniques that produce angiogenic or anti-angiogenic peptides.

C. Fusion Proteins

The present disclosure includes PAMP and PAMP-inhibitor fusion proteins. A fusion protein is a protein comprising two amino acid sequences that are not found joined together in nature. PAMP fusion proteins specifically comprise at least (1) the amino acid sequence shown in SEQ ID NO: 4 or a sequence sharing 90% or 95% sequence identity with SEQ ID NO: 4, and (2) a peptide portion placed at either end of or within the amino acid sequence shown in SEQ ID NO: 4 or sequence sharing 90% or 95% sequence identity with SEQ ID NO: 4. Such PAMP fusion proteins can additionally include other protein elements, such as a linker between such peptide portions.

Fusion proteins are of use, for example, when a protein of interest is present in very small quantities, and protein quantities are insufficient for characterizing the protein, raising antibody against the protein, or utilizing the protein for therapeutic purposes. By fusing a known protein or peptide DNA sequence with the DNA of the protein of interest, fusion proteins (a combination of the protein of interest tagged with the known protein or peptide) can be produced in culture in large quantities.

In certain examples, when attempting to produce a protein of interest, a DNA sequence which codes for the protein of interest is tagged or fused with the sequence for another protein (for example, MBP or GFP) or a sequence that codes for an identifiable peptide (for example, HA or c-Myc). This recombinant DNA is then introduced into a microorganism, which expresses the protein of interest as well as the tagged protein or peptide. To isolate or to localize the protein of interest, the tag, which is now part of the protein, is isolated or localized.

For example, the fusion protein can bind to the appropriate agarose-bound antibody spin column and thus can be separated from all of the other proteins in the culture supernatant or cell lysate. In particular examples, biotinylated anti-MBP, anti-GFP, anti-HA, and anti-c-Myc are used to follow the production of the fusion proteins or to identify the fusion protein in a Western blot format. If the fusion protein is expressed in tissues, the biotinylated antibodies can be used to localize the protein of interest within a tissue section.

In a manner similar to that described GFP and MBP, a DNA sequence coding for a peptide also can be introduced into the DNA sequence of the protein of interest When expressed, this fusion protein contains the epitope of the tag defined by the peptide amino acid sequence. In certain embodiments, agarose bound anti-HA or anti-c-Myc is used to isolate the fusion protein from the culture supernatant or the cell lysate. Biotinylated antibodies are used to identify the proteins of interest in western blots or potentially to localize the fusion proteins in the tissue. These and other methods of creating and detecting fusion proteins are known to those of skill in the art.

VII. Angiogenesis Assays

The following descriptions provide examples of angiogenic assays, which may be useful in measurements of angiogenic activity of, for instance, PAMP, derivatives and analogs of PAMP, and PAMP in the presence of an inhibitor or suspected inhibitor of its angiogenic activity. One of ordinary skill in the art will recognize that other angiogenic assays also can be used.

A. Corneal Pocket Assay

This is the "gold standard" method for following the effect of defined substances to promote neovascularization of the normally avascular cornea. Agents to be tested for angiogenic or anti-angiogenic activity are immobilized in a slow release form in an inert hydron pellet of approximately 1-2 µl volume. That pellet is implanted into the corneal epithelium of an anesthetized C57BL mouse (or a rabbit) in a pocket created by micro-dissection. Over a five to seven day period angiogenic factors stimulate the ingrowth of vessels from the adjacent vascularized corneal limbus. A photographic record is created by slit lamp photography. The appearance, density and extent of these vessels are evaluated and scored. In some cases, the time course of the progression is followed in anesthetized animals, prior to sacrifice. Vessels are evaluated for length, density and the radial surface of the limbus from which they emanate (expressed as clock-faced hours).

B. Intradermal Sponge Angiogenesis Assay

Inert biopolymer sponges impregnated with defined amounts of test reagents are implanted subcutaneously through a transdermal incision, into a pocket created in the subcutaneous tissue. Sponges are then removed following a defined periods ranging from five to fifteen days and the new vessel formation quantitated by a number of biochemical and histomorphometric parameters. Portions of a sponge can be extracted and analyzed by Western blot for endothelial restricted gene product such as VE cadherin, FLK-1 receptors, and others. Frozen section portions of that same sample are evaluated by immunohistochemistry for similar antigens to confirm that expression levels reflect endothelial cell proteins contained within new vessels that have invaded the sponge. In conjunction with the mouse corneal pocket assay, systemic administration of putative angiogenesis inhibitors by intraperitoneal or intravenous routes permits evaluation and comparison of the local effects of those inhibitors on angiogenic stimuli in different microvascular beds.

C. Chick Chorioallantoic Membrane (CAM) Assay

The CAM assay permits the quantitation of angiogenesis and anti-angiogenesis in the chick embryo chorioallantoic membrane (CAM). Briefly, chicken eggs are windowed on day two or three of incubation, and the windows are sealed with tape, wax, glass slides, or PARAFILM. On day eight of incubation, the windows are opened, and small sponges or pieces of gelatin are placed on top of the growing CAM.

After implantation, the sponges are treated with a stimulator (for example, PAMP) or an inhibitor (for example, a PAMP function-blocking antibody) of blood vessel formation. Blood vessels growing vertically into the sponge and at the boundary between sponge and surrounding CAM mesenchyme are counted by a morphometric method on day twelve. Factors that increase the number of blood vessels growing into the sponge are considered angiogenic, whereas factors that inhibit blood vessel growth into the sponge are considered anti-angiogenic. Quantification of the number of new vessels yields a measure of angiogenicity. Thus, this technique facilitates the characteization of agonists or antagonists of angiogenesis. (For more information, see Ribatti et al., *J. Vasc. Res.* 1997, 34:455-463).

D. Directed In Vivo Angiogenesis Assay (DIVAA)

Silicone tubes (0.15 mm outside diameter, New Age Industries, Southampton, Pa.) are cut to 1 cm in length, and one end of each tube is closed with liquid silicone and dried for 24 hours, then autoclaved. A dilution of test substances is prepared in matrigel in sterile cold Eppendorf tubes. Tubes are filled with a Hamilton syringe. Nude mice are anesthetized, and a pocket is made in the dorsal skin of each animal. The tubes are then implanted with the open end first, and the wounds are then sealed.

After nine to eleven days, the tail veins are injected with FITC-dextran to visualize the blood vessels, and the dye is allowed to distribute throughout the vasculature for about 20 minutes. Mice are then euthanized with $CO_2$ and the skin pockets are removed.

Skin is then dissected, keeping the vessels near the mouth of the tube. The matrigel is then displaced from the tube, incubated at 37° C. in the presence of dispase, then vortexed, centrifuged, and matrigel aliquots are transferred into 96-well plates for fluorescent emission. Fluorescence is read in a fluorimeter.

VIII. Pharmaceutical Compositions

The angiogenic and anti-angiogenic peptides and PAMP inhibitors described herein may be formulated in a variety of ways depending on the location and type of disease to be treated or prevented. Pharmaceutical compositions are thus provided for both local use at or near an affected area and for systemic use (in which the agent is administered in a manner that is widely disseminated via the cardiovascular system). This disclosure includes within its scope pharmaceutical compositions including at least one angiogenic peptide (for example, PAMP) or anti-angiogenic peptide, or PAMP inhibitor, formulated for use in human or veterinary medicine. While the angiogenic and anti-angiogenic peptides and PAMP inhibitors typically will be used to treat human subjects, they may also be used to treat similar or identical diseases in other vertebrates, such other primates, dogs, cats, horses, and cows.

Pharmaceutical compositions that include at least one angiogenic or anti-angiogenic peptide or PAMP inhibitor as described herein as an active ingredient, or that include both an angiogenic peptide and an additional angiogenic agent as active ingredients, or that include both an anti-angiogenic peptide or PAMP inhibitor and an additional anti-angiogenic agent, may be formulated with an appropriate solid or liquid carrier, depending upon the particular mode of administration chosen. Additional active ingredients include, for example, angiogenic agents, such as bFGF and VEGF, or anti-angiogenic agents, such as inhibitors of bFGF or VEGF, or protease inhibitors, such as metalloproteinase 2 (MMP2) inhibitors or metalloproteinase 9 (MMP9) inhibitors. Examples of MMP-2 inhibitors include Marinastat (BB-2516) and Batimastat (BB-94) from British Biotechnology, Prinomastat (AG3340) from Aguron, Tanomastat (BAY 12-9566) from Bayer, and BMS-275291 (Bristol Meyers/Squibb). A particular contemplated natural MMP-2 inhibitor is TIMP-2 (tissue inhibitor for metalloproteinase 2), which is known to be specific for MMP-2.

A suitable administration format may best be determined by a medical practitioner for each subject individually. Various pharmaceutically acceptable carriers and their formulation are described in standard formulation treatises, for example, *Remington's Pharmaceutical Sciences* by E. W. Martin. See also Wang and Hanson, *J. Parenteral Sci. Technol.*, Technical Report No. 10, Supp. 42: 2S, 1988.

The dosage form of the pharmaceutical composition will be determined by the mode of administration chosen. For instance, in addition to injectable fluids, inhalational, topical ophthalmic, peritoneal, and oral formulations can be employed. Inhalational preparations can include aerosols, particulates, and the like. In general, the goal for particle size for inhalation is about 1 µm or less in order that the pharmaceutical reach the alveolar region of the lung for absorption. Oral formulations may be liquid (for example, syrups, solutions, or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The compositions or pharmaceutical compositions can be administered by any route, including parenteral administration, for example, intravenous, intramuscular, intraperitoneal, intrasternal or intra-articular injection or infusion, or by sublingual oral, topical, intra-nasal, ophthalmic, or transmucosal administration, or by pulmonary inhalation. When angiogenic or anti-angiogenic peptides or PAMP inhibitors are provided as parenteral compositions, for example, for injection or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. A form of repository or "depot" slow release preparation may be used so that therapeutically effective amounts of the preparation are delivered into the bloodstream over many hours or days following transdermal injection or delivery.

Angiogenic and anti-angiogenic peptides and PAMP inhibitors are also suitably administered by sustained-release systems. Suitable examples of sustained-release formulations include suitable polymeric materials (such as, for example, semi-permeable polymer matrices in the form of shaped articles, for example, films, or mirocapsules), suitable hydrophobic materials (for example as an emulsion in an acceptable oil) or ion exchange resins, and sparingly soluble derivatives (such as, for example, a sparingly soluble salt). Sustained-release angiogenic and anti-angiogenic peptides and PAMP inhibitors may be administered by intravascular, intravenous, intra-arterial intramuscular, subcutaneous, intra-pericardial, or intra-coronary injection. Administration can also be oral, rectal, parenteral, intracisternal, intravaginal, intraperitoneal, topical (as by powders, ointments, gels, drops or transdermal patch), bucal, or as an oral or nasal spray.

Preparations for administration can be suitably formulated to give controlled release of angiogenic and anti-angiogenic peptides and PAMP inhibitors. For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features that allow a controlled release of the active substance. See, for example, U.S. Pat. No. 5,700,486.

In some embodiments, angiogenic or anti-angiogenic peptides or PAMP inhibitors are delivered by way of a pump (see Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution may also be employed. The key factor in selecting an appropriate dose is the result obtained, as measured by increases or decreases in angiogenesis, or by other criteria for measuring control or prevention of disease, as are deemed appropriate by the practitioner. Other controlled release systems are discussed in the review by Langer (*Science* 249:1527-1533, 1990).

In another aspect of the disclosure, angiogenic or anti-angiogenic peptides or PAMP inhibitors are delivered by way of an implanted pump, described, for example, in U.S. Pat. No. 6,436,091; U.S. Pat. No. 5,939,380; and U.S. Pat. No. 5,993,414. Implantable drug infusion devices are used to provide subjects with a constant and long term dosage or infusion of a drug or any other therapeutic agent. Essentially, such device may be categorized as either active or passive.

Active drug or programmable infusion devices feature a pump or a metering system to deliver the drug into the patient's system. An example of such an active drug infusion device currently available is the Medtronic SynchroMed™ programmable pump. Such pumps typically include a drug reservoir, a peristaltic pump to pump the drug out from the reservoir, and a catheter port to transport the pumped out drug from the reservoir via the pump to a patient's anatomy. Such devices also typically include a battery to power the pump, as well as an electronic module to control the flow rate of the pump. The Medtronic SynchroMed™ pump further includes an antenna to permit the remote programming of the pump.

Passive drug infusion devices, in contrast, do not feature a pump, but rather rely upon a pressurized drug reservoir to deliver the drug. Thus, such devices tend to be both smaller as well as cheaper as compared to active devices. An example of such a device includes the Medtronic IsoMed™. This device delivers the drug into the patient through the force provided by a pressurized reservoir applied across a flow control unit.

The implanted pump can be completely implanted under the skin of a subject, thereby negating the need for a percutaneous catheter. These implanted pumps can provide the patient with angiogenic or anti-angiogenic peptides or PAMP inhibitors at a constant or a programmed delivery rate. Constant rate or programmable rate pumps are based on either phase-change or peristaltic technology. When a constant, unchanging delivery rate is required, a constant-rate pump is well suited for long-term implanted drug delivery. If changes to the infusion rate are expected, a programmable pump may be used in place of the constant rate pump system. Osmotic pumps may be much smaller than other constant rate or programmable pumps, because their infusion rate can be very low. An example of such a pump is described listed in U.S. Pat. No. 5,728,396.

For oral administration, the pharmaceutical compositions can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring, and sweetening agents as appropriate.

For administration by inhalation, the compounds for use according to the present disclosure are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

For topical administration, the compounds for use are, for example, mixed with ethanol, methanol, propylene glycol, or dimethyl sulfoxide, which act as a vehicle to facilitate uniform distribution of the compound to a target area of the subject's body, such as a wound or decubitus ulcer.

Pharmaceutical compositions that comprise an angiogenic or anti-angiogenic peptide or PAMP inhibitor as described herein as an active ingredient will normally be formulated with an appropriate solid or liquid carrier, depending upon the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

For example, for parenteral administration, angiogenic or anti-angiogenic peptides or PAMP inhibitors can be formulated generally by mixing them at the desired degree of purity, in a unit dosage injectable form (solution, suspension, or emulsion), with a pharmaceutically acceptable carrier, for instance, one that is non-toxic to recipients at the dosages and concentrations employed and is compatible with other ingredients of the formulation. A pharmaceutically acceptable carrier is a non-toxic solid, semisolid or liquid filler, diluent, encapsulating material or formulation auxiliary of any type.

Generally, the formulations are prepared by contacting the angiogenic or anti-angiogenic peptides or PAMP inhibitors each uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-queous vehicles such as fixed oils and ethyl oleate are also useful herein, as well as liposomes.

The pharmaceutical compositions that comprise an angiogenic or anti-angiogenic peptide or PAMP inhibitor, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The therapeutically effective amount of angiogenic or anti-angiogenic peptide or PAMP inhibitor will be dependent on the peptide or inhibitor utilized, the subject being treated, the severity and type of the affliction, and the manner of administration. Because PAMP is one million times more potent than other known angiogenic factors, such as bFGF and VEGF, the dose administered is, in some embodiments, substantially lower than that required for other angiogenic factors. For example, a therapeutically effective amount of PAMP or PAMP inhibitor can vary from about 0.1 nM per kilogram (kg) body weight to about 1 μM per kg body weight, such as about 1 nM to about 500 nM per kg body weight, or about 5 nM to about 50 nM per kg body weight. The exact dose is readily determined by one of skill in the art based on the potency of the specific compound, the age, weight, sex and physiological condition of the subject.

The peptides of the present disclosure (for example, PAMP and PAMP inhibitors) also can be administered as naked DNA encoding the peptide. To simplify the manipulation and handling of the nucleic acid encoding the peptide, the nucleic acid is generally inserted into a cassette, where it is operably linked to a promoter. Preferably, the promoter is capable of driving expression of the protein in cells of the desired target tissue. The selection of appropriate promoters can readily be accomplished. Preferably, the promoter is a high expression promoter, for example the 763-base-pair cytomegalovirus (CMV) promoter, the Rous sarcoma virus (RSV) promoter (Davis, et al., *Hum. Gene. Ther.* 4:151, 1993), or the MMT promoter.

Other elements that enhance expression also can be included, such as an enhancer or a system that results in high levels of expression, such as a tat gene or tar element. This cassette is inserted into a vector, for example, a plasmid vector such as pUC118, pBR322, or other known plasmid vector, that includes, for example, an *E. coli* origin of replication. See, Sambrook, et al., *Molecular Cloning: A Laboratory Manual,* Cold Spring Harbor Laboratory press, (1989). The plasmid vector may also include a selectable marker such as the β-lactamase gene for ampicillin resistance, provided that the marker polypeptide does not adversely effect the metabolism of the organism being treated. The cassette also can be bound to a nucleic acid binding moiety in a synthetic delivery system, such as the system disclosed in WO 95/22618.

Optionally, the DNA may be used with a microdelivery vehicle such as cationic liposomes and adenoviral vectors. (For a review of the procedures for liposome preparation, targeting and delivery of contents, see Mannino and Gould-Fogerite, *BioTechniques*, 6:682, 1988); Feigner and Holm, *Bethesda Res. Lab. Focus*, 11(2):21, 1989); and Maurer, *Bethesda Res. Lab. Focus*, 11(2):25, 1989). Replication-defective recombinant adenoviral vectors can be produced in accordance with known techniques. (See Quantin, et al., *Proc. Natl. Acad. Sci USA*, 89:2581-2584, 1992; Stratford-Perricadet, et al., *J. Clin. Invest.*, 90:626-630, 1992; and Rosenfeld, et al., *Cell*, 68:143-155, 1992).

The effective dose of the nucleic acid will be a function of the particular expressed protein, the target tissue, the subject, and his or her clinical condition. Effective amounts of DNA are between about 1 and 4000 μg, or about 1000 and 2000, or between about 2000 and 4000. In certain situations, it is desirable to use nucleic acids encoding two or more different proteins in order to optimize the therapeutic outcome. For example, DNA encoding PAMP peptide and another angiogenic protein, for example, VEGF or bFGF, can be used. Alternatively, DNA encoding PAMP can be combined with other genes or their encoded gene products to enhance the activity of targeted cells, while simultaneously inducing angiogenesis, including, for example, nitric oxide synthase, L-arginine, fibronectin, urokinase, plasminogen activator and heparin.

In order to facilitate injection, the nucleic acid is formulated with a pharmaceutically acceptable carrier. Examples of suitable carriers include, saline, albumin, dextrose and sterile water. The nucleic acid is injected into the ischemic tissue using standard injection techniques by use of, for example, a hypodermic needle, for example a hypodermic needle size between No. 29 and No. 16. The nucleic acid also may be injected by an externally applied local injection apparatus, such as that used to inject antigens for allergy testing; or a trascutaneous "patch" capable of delivery to subcutaneous muscle. The nucleic acid is injected at one site, or at multiple sites throughout the ischemic tissue.

Once injected, the nucleic acid capable of expressing the desired angiogenic protein is taken up and expressed by the cells of the tissue. Because the vectors containing the nucleic acid of interest are not normally incorporated into the genome of the cells, expression of the protein of interest takes place for only a limited time. Typically, the angiogenic protein is only expressed in therapeutic levels for about two days to several weeks, preferably for about one to two weeks. Reinjection of the DNA can be utilized to provide additional periods of expression of the angiogenic protein. If desired, use of a retrovirus vector to incorporate the heterologous DNA into the genome of the cells will increase the length of time during which the therapeutic polypeptide is expressed, from several weeks to indefinitely.

Expression of the angiogenic protein and its secretion from the tissue cells induces angiogenesis, allowing for the treatment of ischemia and thus diseases such as peripheral vascular disease, cerebral ischemia, or coronary artery disease.

IX. Therapeutic Uses

A. Methods of Treating Disease or Condition with PAMP

Methods are disclosed herein for promoting angiogenesis in an area in a subject who has or is at risk for developing coronary artery disease, cerebral ischemia, a wound, or peripheral vascular disease. The methods include introducing a therapeutically effective amount of proadrenomedullin N-terminal 20 peptide (PAMP) to the area being treated, thereby promoting angiogenesis in the subject. In some embodiments, PAMP is ad administered as naked DNA encoding the peptide, using for instance protocols used for delivering VEGF to ischemic tissues (see, for example, Isner, et al, *J. Vasc. Surg.*, 1998; 28:964-975; Losardo et al., *Circulation*, 1998; 98:2800-2804).

In some embodiments, the PAMP peptide or peptide-encoding DNA is admniistered locally to the affected area, for example by direct topical administration to a wound or other lesion in which neovascularization is desired, or is parenterally directed to an affected area, such as an ischemic extremity. For subjects with peripheral vascular disease, administration is, for example, by direct topical administration to a wound, or by intra-arterial, intravenous, subcutaneous, or intramuscular injection into the affected limb. Efficacy of the treatment is shown, for example, by a regression of symptoms, for example, a lessening of cramping in the leg or arm, or a lessening of claudication, numbness, tingling, weakness, or pain, or healing of skin ulcers on the limb. An improvement in vascular function is also demonstrated, for example, by increased skin temperature or a color change in the skin of the limbs.

For subjects with cerebral ischemia, administration is, for example, by intra-arterial or intrathecal injection, or by direct injection of ischemic brain areas. Intra-arterial injection can be directed to ischemic regions, for example, by injection into the basilar artery to administer the agent to the occipital cortex. In some embodiments, administration is by intravenous or intra-arterial injection following osmotic disruption of the blood brain barrier (see, for example, U.S. Pat. No. 5,124,146). In some embodiments, administration is, for example, by injection into the basilar, carotid, or cerebral arteries. Efficacy of the treatment is indicated, for example, by an abatement of symptoms, for example, a lessening of numbness or weakness of the face, arm or leg, lessening of confusion, improvement in speaking, visual improvement, or improvement in walking, balance, or coordination.

For subjects with coronary artery disease, administration is, for example, by intra-arterial (particularly intracoronary), or intrapericardial injection. In some embodiments, the PAMP protein or peptide-encoding DNA is administered systemically, such as by intravenous injection. Efficacy of treatment is demonstrated, for example, by a regression of symptoms, for example chest pressure or pain.

For subjects with a wound, administration is, for example, by subcutaneous or intravenous injection, by direct injection of the wound, or by topical application. Efficacy of the treatment is determined, for example, by an improvement in wound healing.

Administration may begin whenever a subject has developed, or is at risk for developing cerebral ischemia, coronary artery disease, or peripheral vascular disease, or when symptoms of reduced blood flow to the brain, heart, or one or more limbs are present, such as chest or limb pain, or neurological symptoms, such as dizziness, confusion, loss of speech, or loss of mobility.

Combinations of angiogenic factors are also of use. For example, PAMP peptide or peptide-encoding DNA is administered in conjunction with bFGF or VEGF protein or protein-encoding DNA.

An effective amount of PAMP peptide or peptide-encoding DNA can be administered in a single dose, or in multiple doses, for example hourly, daily, or weekly during a course of treatment.

B. Methods of Treating Disease or a Condition with PAMP Inhibitors

Methods are disclosed herein for inhibiting angiogenesis in an area in a subject who has or is at risk for developing a tumor, retinopathy, psoriasis, endometriosis, or arthritis. The methods include introducing a therapeutically effective amount of a PAMP inhibitor to the area, thereby inhibiting angiogenesis in the subject. In some embodiments, the PAMP inhibitor is administered as naked DNA encoding the peptide inhibitor using protocols used for delivering VEGF to ischemic tissues (see, for example, Isner, et al., *J. Vasc. Surg.*, 28:964-975, 1998; Losardo et al., *Circulation*, 98:2800-2804, 1998).

In one embodiment, the PAMP inhibitor or inhibitor peptide-encoding DNA is administered locally. For subjects with a tumor, administration is, for example, by intra-arterial injection to the tumor's arterial supply, or by direct injection into the tumor. Other routes of administration will be determined by the tumor location. Ovarian tumors are, for example, treated by intraperitoneal washing with the inhibitor. A brain tumor is, for example, treated by intra-arterial or intrathecal injection, by intranasal administration, by direct injection of affected brain areas, or by intravenous or intra-arterial injection following osmotic disruption of the blood brain barrier (see, for example, U.S. Pat. No. 5,124,146). Lung cancer is treated, for example, by direct injection of the tumor, by inhalation, or infusion into the lobar circulation of an affected lobe of the lung. Efficacy of the treatment is determined, for example, by monitoring tumor burden, or is indicated, for example, by a lessening of symptoms, such as pain.

For subjects with retinopathy, administration is, for example, by intra-ocular injection (for example, into the posterior chamber of the eye), or by topical ophthalmic administration. Alternatively, the agent may be administered intravascularly, for example into the vascular supply for the retinal artery. Efficacy of the treatment is determined, for example, by an improvement in vision, by a stabilization of vision, by a lack of new blood vessel formation in the retina, or by failure of the disease to progress.

For subjects with psoriasis, administration is, for example, by subcutaneous or intravenous injection, or by topical application. Efficacy of the treatment is determined, for example, by an abatement of psoriasis symptoms.

For subjects with arthritis, administration is, for example, by intra-articular injection. Efficacy of the treatment is monitored, for example, by detecting an improvement in mobility, or a lessening of joint pain.

For subjects with endometriosis, administration is, for example, by direct injection of the endometrial growths, or by intraperitoneal washing with the PAMP inhibitor. Efficacy of the treatment is shown, for example, by an improvement in mobility, or a lessening of pelvic pain.

Administration of the inhibitor may begin whenever a subject has developed, or is at risk for developing a tumor, retinopathy, psoriasis, or endometriosis, or when symptoms of inappropriate neovascularization are present.

Combinations of PAMP inhibitors with other anti-angiogenic factors are also of use. For example, PAMP inhibitor or inhibitor peptide-encoding DNA is administered in conjunction with bFGF or VEGF inhibitor, such as SU5416, which is a specific VEGF-R antagonist, and SU6668 which blocks the receptors for VEGF, bFGF, and PDGF (see, for example, Liu et al., *Seminars in Oncology* 29 (Suppl 11): 96-103, 2002; Shepherd et al., *Lung Cancer* 34:S81-S89, 2001).

An effective amount of PAMP inhibitor or inhibitor peptido-encoding DNA can be administered in a single dose, or in multiple doses, for example daily, weekly, every two weeks, or monthly during a course of treatment.

The disclosure is illustrated by the following non-limiting Examples.

EXAMPLES

Example 1

Comparison of the Angiogenic Potential of Vascular Endothelial Growth Factor (VEGF), Adrenomedullin (AM), and Proadrenomedullin N-Terminal 20 Peptide (PAMP)

This example provides a description of use of the Directed in vivo Angiogenesis Assay (DIVAA; see Martinez et al., *J. Natl. Cancer Inst.* 2002; 94:1226-1237) to measure the angiogenic potential of PAMP in comparison to known angiogenesis factors.

A. Preparation of Implants

Implants were prepared as follows: Silicone tubes (0.15 mm outside diameter, New Age Industries, Southampton, Pa.) were cut to 1 cm in length. One end of each tube was closed with liquid silicone and dried for 24 hours to allow fumes to diffuse out. Tubes were then autoclaved.

A dilution of test substances was prepared in matrigel in sterile cold Eppendorf tubes. A stock of 25× was prepared to avoid diluting the matrigel too much. Tubes were filled with a Hamilton syringe. All the material was kept sterile and cold. Each tube required 18-20 µl. The matrigel was allowed to solidify at 37° C. for at least 30 minutes.

B. Surgical Procedure

Nude mice were anesthetized with Ketamine and Xylazine (1:4 ratio), 50 µl per mouse, intradermally. A pocket was made in the dorsal skin of each animal with scissors. The tubes were implanted with the open end first. The wounds were then sealed with surgical clips. Mice were kept warm until they recovered consciousness. Mice were then maintained for nine to eleven days.

C. Quantitation of Angiogenesis

Mice were placed under a heating lamp to dilate their tail veins. Tail veins were injected with 25 mg/ml FITC-dextran (Sigma), 100 µl mouse. After about 20 minutes, the dye had been distributed. Mice were then euthanized with $CO_2$ and the skin pockets were removed and kept in a PBS-wet cloth.

Skin was then dissected out, keeping the vessels near the mouth of the tube. The tube was placed an eppendorf tube containing 300 µl dispase (Collaborative Biomedical Products). Then the matrigel was displaced from the tube; these were frozen until they were needed later.

Matrigels were thawed and incubated at 37° C. for one hour, then vortexed, centrifuged, and 100 µl was transferred into a 96-well plate for fluorescent emission (black sides). Excitation for FITC was 485 nm. Emission was 535 nm. Fluorescence was read in a fluorometer.

D. Results

Figure 2:
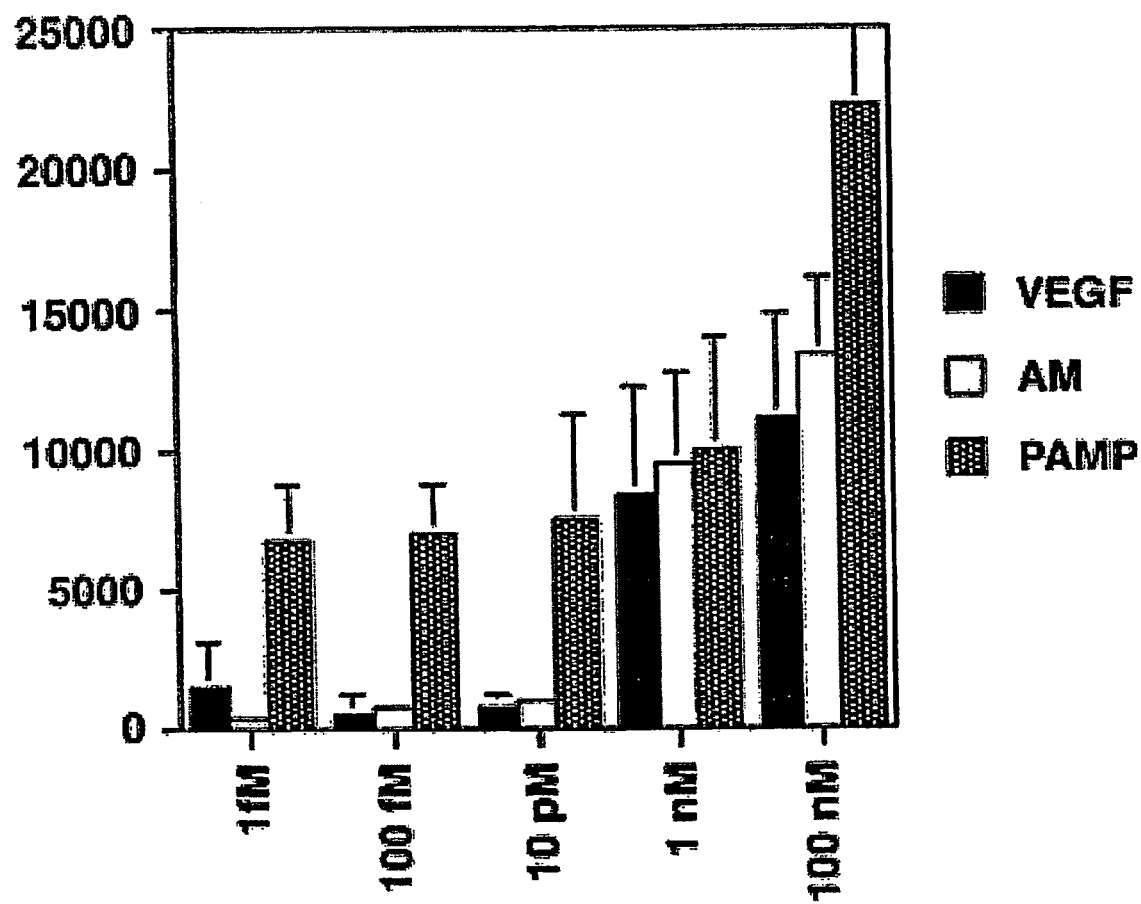
FIG. 2 is a graph showing that PAMP promotes angiogenesis in a DIVAA assay.

As shown in Table 2, FIG. 1, and FIG. 2, PAMP was a significantly more potent angiogenic factor than either VEGF or AM.

TABLE 2

| Concentration | VEGF | AM | PAMP |
| --- | --- | --- | --- |
| 1 fM | 1563.2 ± 1643 | 496 ± 275 | 6837.6 ± 1982 |
| 100 fM | 571 ± 785 | 787 ± 130 | 7044 ± 1727 |
| 10 pM | 863.4 ± 437 | 1033.2 ± 343 | 7611.2 ± 3747 |
| 1 nM | 8435 ± 3931 | 9590 ± 3164 | 10122.2 ± 3970 |
| 100 nM | 11206 ± 3735 | 13490 ± 2731 | 22283.6 ± 6746 |

Values represent mean ± standard deviation of five implants expressed as arbitrary fluorescence units.

Example 2

PAMP is a Potent Angiogenic Factor and its Inhibition Results in Reduction of Tumor Growth This example demonstrates that PAMP is a very potent angiogenic factor, being able to induce neovascularization in animal models at concentrations six orders of magnitude lower than other classic proangiogenic factors such as VEGF and AM. This example also demonstrates that human microvascular endothelial cells have receptors for PAMP and respond to it by increasing their migration and cord formation in matrigel assays. In addition, this example shows that PAMP stimulation induces expression of classic angiogenic factors in endothelial cells, and that the carboxy-terminal peptide fragment PAMP(12-20) acts as an inhibitor of PAMP-induced angiogenesis and is able to delay tumor growth in xenograft models of tumor progression.

A. Experimental Procedures

Chemicals

Synthetic human AM, PAMP, and PAMP(12-20) were purchased from Bachem. Recombinant human VEGF and bFGF were obtained from R&D Systems.

Chick Embryo Aortic Arch Assay

The chick embryo aortic arch assay is an ex vivo angiogenesis assay that was performed as previously described (Isaacs, et al., *J. Biol. Chem.*, 16;277(33):29936-44, 2002; Auerbach et al., *Clin. Chem.* 49, 32-40, 2003). Briefly, aortic rings of approximately 0.8 mm in length were prepared from the five aortic arches of 13 day-old chicken embryos (Truslow Farms) and the soft connective tissue of the adventitia layer was carefully removed with tweezers. Each aortic ring was placed in the center of a well in a 48-well plate and covered with 10 µl matrigel (BD Biosciences). After the matrigel solidified, 300 µl of growth factor-free human endothelial-SFM basal growth medium (Invitrogen) containing the proper concentration of the test substances were added to each well. The plates were kept in a humid incubator at 37° C. in 5% $CO_2$ for 24-36 hours. Microvessels sprouting from each aortic ring were photographed in an inverted microscope and the area covered by the newly formed capillaries was estimated by image analysis.

Directed In Vivo Angiogenesis Assay (DIVAA)

Analysis and quantitation of angiogenesis was done using DLVAA as previously described (Martinez et al., *J. Natl. Cancer Inst.*, 21;94(16):1226-37, 2002; Guédez et al., *Am. J. Pathol.* 162, 143 1-1439, 2003). Briefly, 10 mm long surgical-grade silicone tubes with only one end open (angioreactors) were filled with 20 µl of matrigel alone or mixed with AM, bFGF, VEGF, PAMP, and/or PAMP(12-20) at the indicated concentrations. Human lung cancer cell lines (see below) were also premixed with matrigel alone or in combination with PAMP(12-20) at 10,000 cells per angioreactor. After the matrigel solidified, the angioreactors were implanted into the dorsal flanks of anesthetized athymic nude mice (NCI colony). After eleven days, the mice were injected intravenously with 25 mg/ml FITC-dextran (100 µl/mouse, Sigma) 20 minutes before removing the angioreactors. Photographs of the implants were taken for visual examination of angiogenic response. Quantitation of neovascularization in the angioreactors was determined as the amount of fluorescence trapped in the implants and was measured in a HP Spectrophotometer (Perkin Elmer).

The human cancer cell lines used, A549 and H1299, were obtained from the American Tissue Culture Collection (ATTC) and fed with RPMI164O containing 10% fetal bovine serum (Invitrogen). Before they were used in animals, both cell lines were tested for a panel of human and murine pathogens and found to be pathogen-free.

Calcium Measurements

Human dermal microvascular endothelial cells were obtained from Cell Applications, Inc. and cultured in 96-well plates at $1.0 \times 10^5$ cells per well. The cells were loaded for 60 minutes at room temperature with the fluorescent dye FLIPR (Molecular Devices) and then transferred to the FlexStation II (molecular Devices) for analysis. The test compounds were prepared in another plate at a concentration of 5× and were added to the proper wells by the robotic arm of the FlexStation II. Fluorescence was measured every five seconds in each well and recorded. One mM ATP (Sigma) was used as a calcium agonist (Lau et al., *Life Sci.* 73, 20 19-2028, 2003).

Proliferation Assay

The same microvascular endothelial cells were seeded in 96-well plates at a density of $2.0 \times 10^5$ cells per well in serum-free medium containing different concentrations of the test peptides. After three days in culture, the number of viable cells per well was estimated by the MTT assay as reported (Iwai et al., *Lung Cancer* 23, 209-222, 1999). Results are represented as percentage growth over the untreated control.

Migration Assay

Cell motility was measured as described (Martinez et al., *J. Natl. Cancer Inst.*, 21;94(16):1226-37, 2002). Test peptides were placed at various concentrations at the bottom of a ChemoTx chamber (NeuroProbe Inc.). The intermediate membrane was coated with 10 µg/ml fibronectin, and in the upper chamber $5.0 \times 10^5$ human endothelial cells were added. After a four hour incubation at 37° C., the membrane was fixed and stained (Protocol Hema3, Biochemical Sciences Inc.). The cells trapped in the porous membrane were photographed through a 25× microscope objective and the number of cells per photographic field was counted.

Cord Formation Assay

Human endothelial cells were seeded at $2.0 \times 10^5$ cells per well over a solid layer of matrigel covering the bottom of a 24-well plate in the presence or absence of the test peptides as described (Nam et al., *Phytother. Res.* 17, 107-111). After an overnight incubation, the tubular structures were photographed (three pictures per well) and the number of knots per photographic field were counted as a measure of lattice complexity.

Real-Time PCR Quantification of Gene Expression

Human endothelial cells were cultured in T-75 flasks at a density of $2.5 \times 10^6$ cells/well. After the cells were attached to the bottom of the plate, they were treated with 10 nM PAMP in serum-free medium for 24 hours. At the end of this exposure, the cells were washed once with PBS, scraped from the plate and their total RNA was extracted using the RNeasy Mini Kit from Qiagen and reverse transcribed using the SuperScript First-Strand Synthesis system (Invitrogen). Quantification of gene expression was performed by real-time PCR as described (Martinez et al., *J. Endocrinol.* 176, 95-102, 2003). The PCR reaction was run in an Opticon cycler (MJ Research) using Sybr Green PCR master mix (Applied Biosystems). Thermocycling was performed in a final volume of 25 µl containing 2 µl of cDNA (1:10 dilution) and 400 nM of primers (see below). All targets were amplified in triplicates in the same run as the house-keeping gene, using the following cycle scheme: after initial denaturation of the samples at 95° C. for 2 minutes, 46 cycles of 95° C. for 30 seconds, 60° C. for 30 seconds, and 72° C. for 30 seconds were performed.

Fluorescence was measured in every cycle and mRNA levels were normalized by the 18S RNA values in all samples. A melting curve was run after PCR by increasing temperature from 50° C. to 96° C. (0.5° C. increments). A single peak was obtained for all amplicons, thus confirming the specificity of the reaction Primers were as follows:

```
AM forward:
ACA TGA AGG GTG CCT CTC GAA        (SEQ ID NO: 7)

AM reverse:
AGG CCC TGG AAG TTG TTC ATG        (SEQ ID NO: 8)

VEGF forward:
TCA GAG CGG AGA AAG CAT TTG T      (SEQ ID NO: 9)

VEGF reverse:
TCG GCT TGT CAC ATC TGC AA         (SEQ ID NO: 10)

bFGF forward:
CGA CCC TCA CAT CAA GCT ACA AC     (SEQ ID NO: 11)

bFGF reverse:
CCA GTT CGT TTC AGT GCC ACA T      (SEQ ID NO: 12)

PGDF A forward:
TTC GGA GGA AGA GAA GCA TCG        (SEQ ID NO: 13)

PGDF A reverse:
GCA CTT GAC ACT GCT CGT GTT G      (SEQ ID NO: 14)

PDGF B forward:
AAC AAC CGC AAC GTG CAG T          (SEQ ID NO: 15)

PDGF B reverse:
TCT CGA TCT TTC TCA CCT GGA C      (SEQ ID NO: 16)

PDGF C forward:
TTG AGG AAC CCA GTG ATG GAA C      (SEQ ID NO: 17)

PDGF C reverse:
CAG CTT CTG TGA ATT GTG GCA T      (SEQ ID NO: 18)

18 S RNA forward:
ATG CTC TTA GCT GAG TGT CCC G      (SEQ ID NO: 19)

18 5 RNA reverse:
ATT CCT AGC TGC GGT ATC CAG G      (SEQ ID NO: 20)
```

Xenograft Experiment

Twenty female athymic nude mice from the NIH colony in Frederick (MD) were injected subcutaneously with $1.0 \times 10^7$ A549 cells/mouse. Two weeks later, all the mice had developed palpable tumors under the skin and at this time they were divided in two groups. Three times a week, each individual tumor was measured (length, height, thickness) and every mouse received an intratumoral injection, according to their group. Group 1 (control) received 100 µl PBS. Group 2 received 100 µl 1 µM PAMP(12-20) in PBS. When the tumor burden became unbearable, the mice were sacrificed.

Statistical Analysis

When appropriated, data were compared by two-tailed Student's t test. P values lower than 0.05 were considered statistically significant.

B. Angiogenic Potential of PAMP in Ex Vivo and In Vivo Assays

Figure 3:
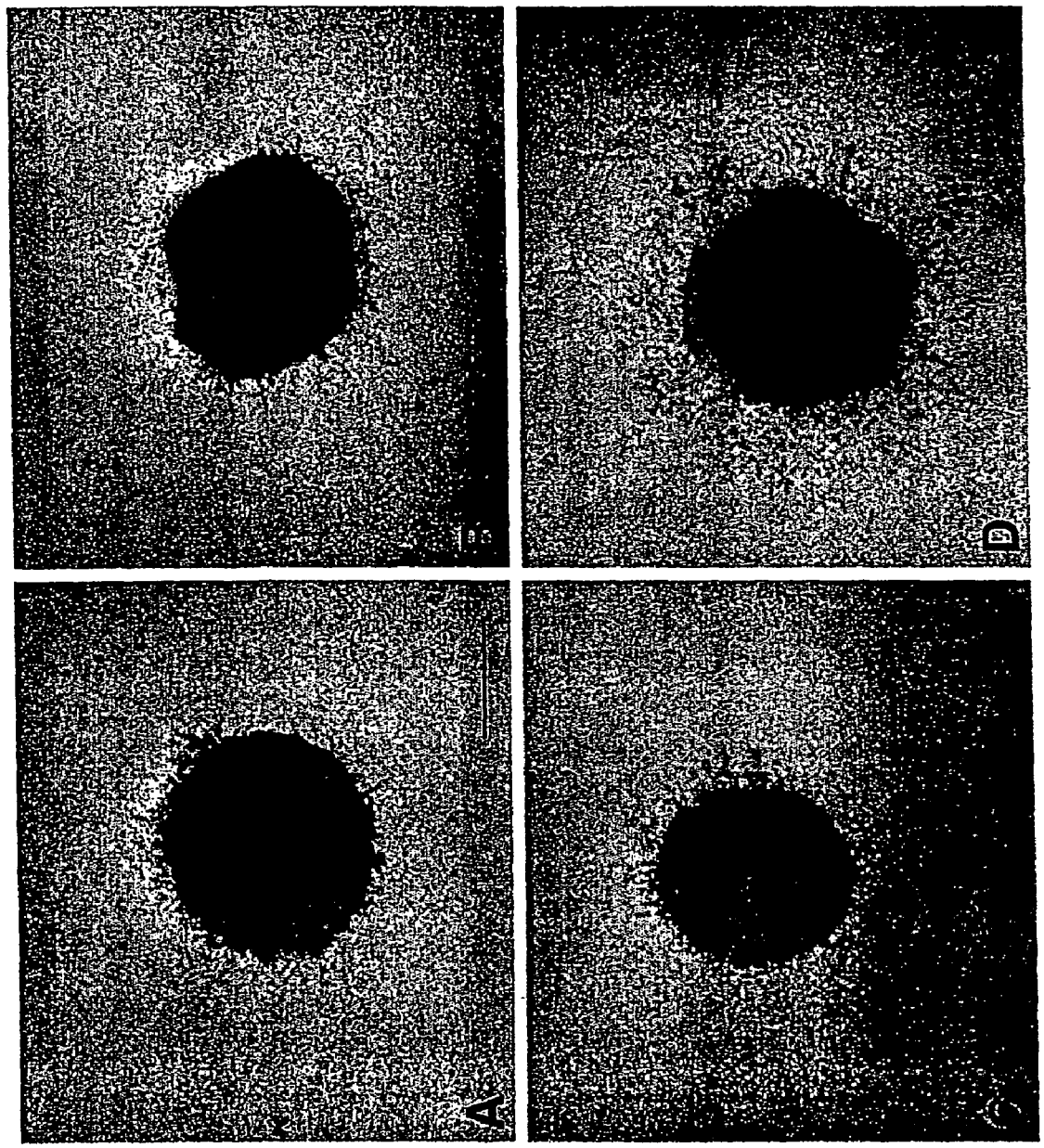
FIG. 3A-D is a set of digital images showing the comparative angiogenic potential of AM, VEGF, and PAMP in the chick embryo aortic ring assay. Aortic rings were embedded in matrigel and exposed to serum-free medium containing either PBS as a negative control (FIG. 3A), or 1 nM of the peptides AM (FIG. 3B), VEGF (FIG. 3C), or PAMP (FIG. 3D). Only in the case of PAMP was the crown of sprouting new vessels larger than the control. Bar=0.5 mm.

There are many ways of testing angiogenesis (Auerbach et al., *Clin. Chem.* 49, 32-40, 2003) and this example makes use of the chick embryo aortic arch assay for a preliminary assessment of the angiogenic properties of PAMP. Regular angiogenic molecules such as AM and VEGF were able to induce a statistically significant increase of sprouting blood vessels over untreated controls at concentrations of 100 nM and higher. By comparison, PAMP was able to induce growth of numerous blood vessels at concentrations as low as 1 nM, whereas AM and VEGF at this concentration do not promote any significant proliferation over the control (FIG. 3A). This initial observation indicates that PAMP is a far more potent proangiogenic factor than previously described molecules.

Figure 4:
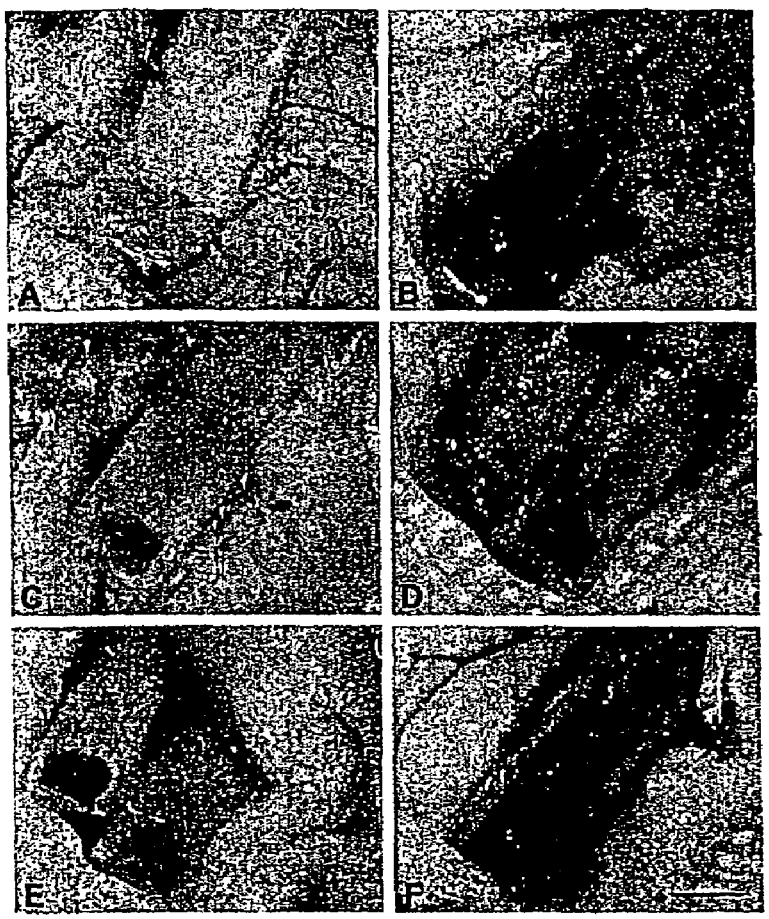
FIG. 4A-G is a set of digital images and a graph showing the angiogenic potential in vivo of AM, VEGF, and PAMP as compared by the DIVAA assay. Silicone capsules containing different concentrations of the peptides in matrigel were implanted under the skin of nude mice for 11 days.
Figure 4:
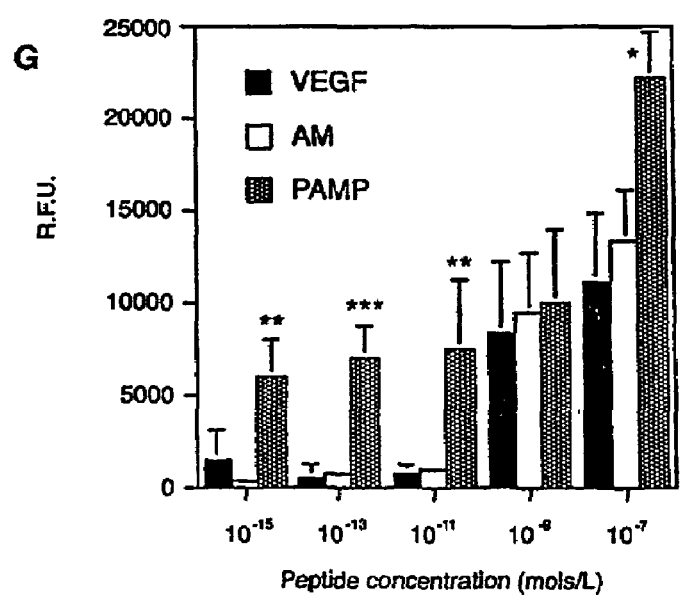

To further characterize this observation, an in vitro assay was employed that allows for more precise quantitation of angiogenic properties: the directed in vitro angiogenesis assay or DIVAA (Martinez et al., *J. Natl. Cancer Inst.*, 21;94 (16):1226-37, 2002; Guédez et al., *Am.]. Pathol.* 162, 143 1-1439, 2003). The assay involves implanting small silicone capsules carrying the test substances under the skin of nude mice. After eleven days, the mice are injected with a specific amount of FITC-dextran, and the volume of blood circulating through the implant is quantified by measuring the fluorescence in the capsule. In addition, the new blood vessels growing into the silicone tube can be seen directly by transparency (FIG. 4A-F). Interestingly, PAMP was able to elicit an angiogenic response at concentrations as low as 1 femtomols/L (FIG. 4C). The extent of the angiogenic response can be seen clearly when this response is compared with the negative control (FIG. 4A). The angiogenic response elicited by PAMP was dose-dependent (FIG. 4C-G). When compared to and VEGF responses at equimolar concentrations, a clear difference was observed. In this animal model, AM and VEGF began to induce angiogenesis at nanomolar concentrations, whereas PAMP was already active in the femtomolar range (FIG. 4G).

C. PAMP Receptors are Present in Endothelial Cells

Figure 5:
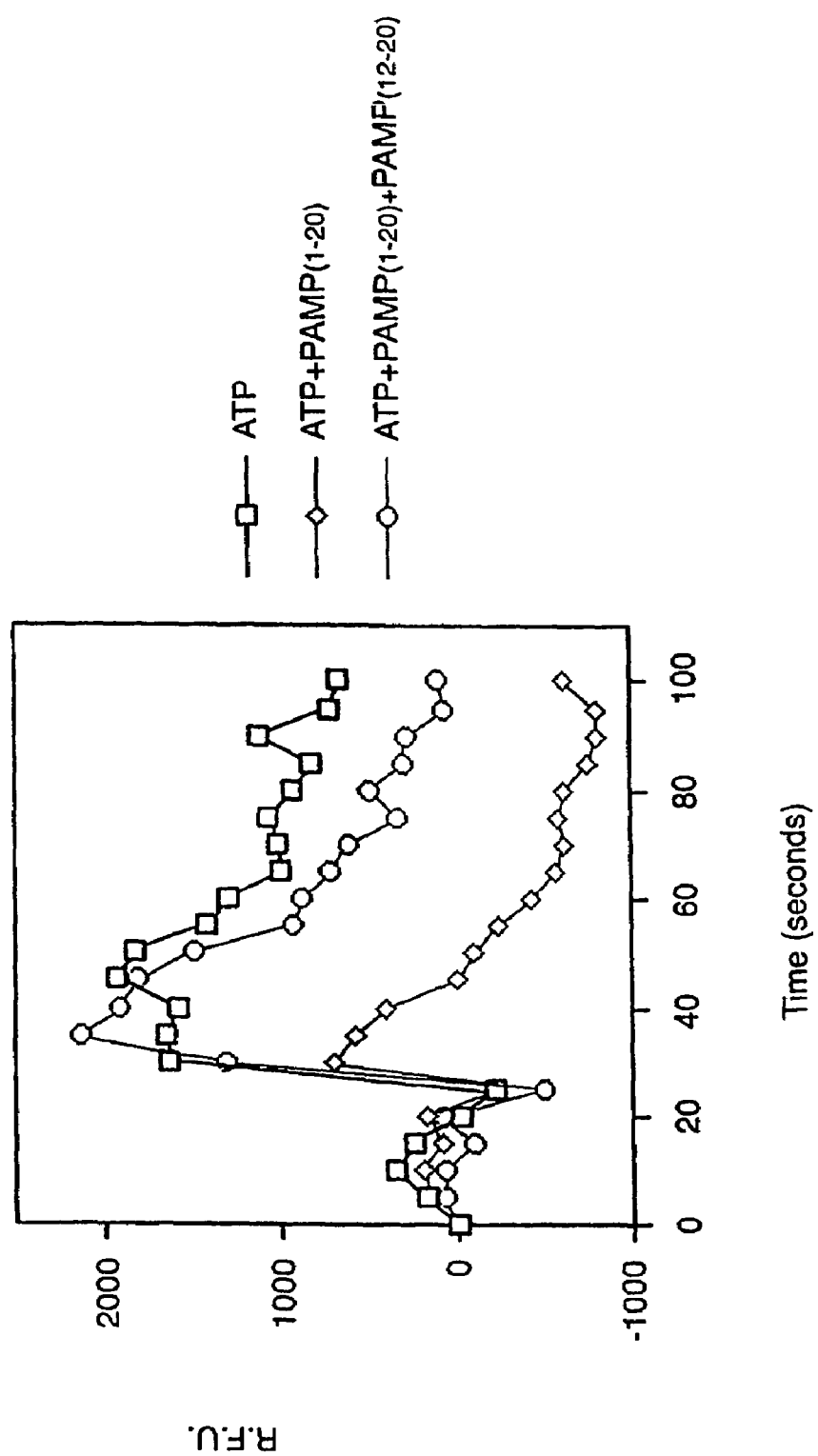
FIG. 5 is a graph showing that a PAMP receptor is present in human microvascular endothelial cells. Addition of 1 mM ATP induces an increase in calcium flux in endothelial cells (squares), whereas addition of 10 nM full-length PAMP greatly reduces this effect (diamonds). This blocking effect was reversed by 100 nM PAMP(12-20) (circles). R.F.U=Relative fluorescence units.

Although the AM receptor has been well characterized at the molecular level (McLatchie et al., *Nature* 393, 333-339, 1998), the structure of the PAMP receptor is not yet available. Nevertheless, exposure of adrenal medulla cells to PAMP results in a decrease of carbachol-induced calcium influx (Katoh et al, *J. Neurochem.* 64, 459-461, 1995). To create similar conditions in endothelial cells, cells were stimulated with 1 mM ATP, a well known transient agonist of calcium influx in these cells (Lau et al., *Life Sci.* 73, 20 19-2028, 2003), obtaining a typical response (FIG. 5, squares). This response was greatly reduced by the presence of 10 nM PAMP in the medium (FIG. 5, diamonds). The peptide fragment PAMP(12-20) has been shown to have opposite actions to full-length PAMP in blood pressure regulation (Fry et al.,

*Life Sci.* 60, PL161-167, 1997), suggesting its potential utility as a PAMP antagonist. To demonstrate the specificity of the inhibition, an excess of the PAMP peptide fragment was added and the initial response was recovered (FIG. 5, circles). Taken together, these data show that there is a functional PAMP receptor in the membrane of the endothelial cells, and therefore this peptide may activate directly the angiogenic response described above.

D. Physiological Effects of PAMP on Endothelial Cells

Figure 6:
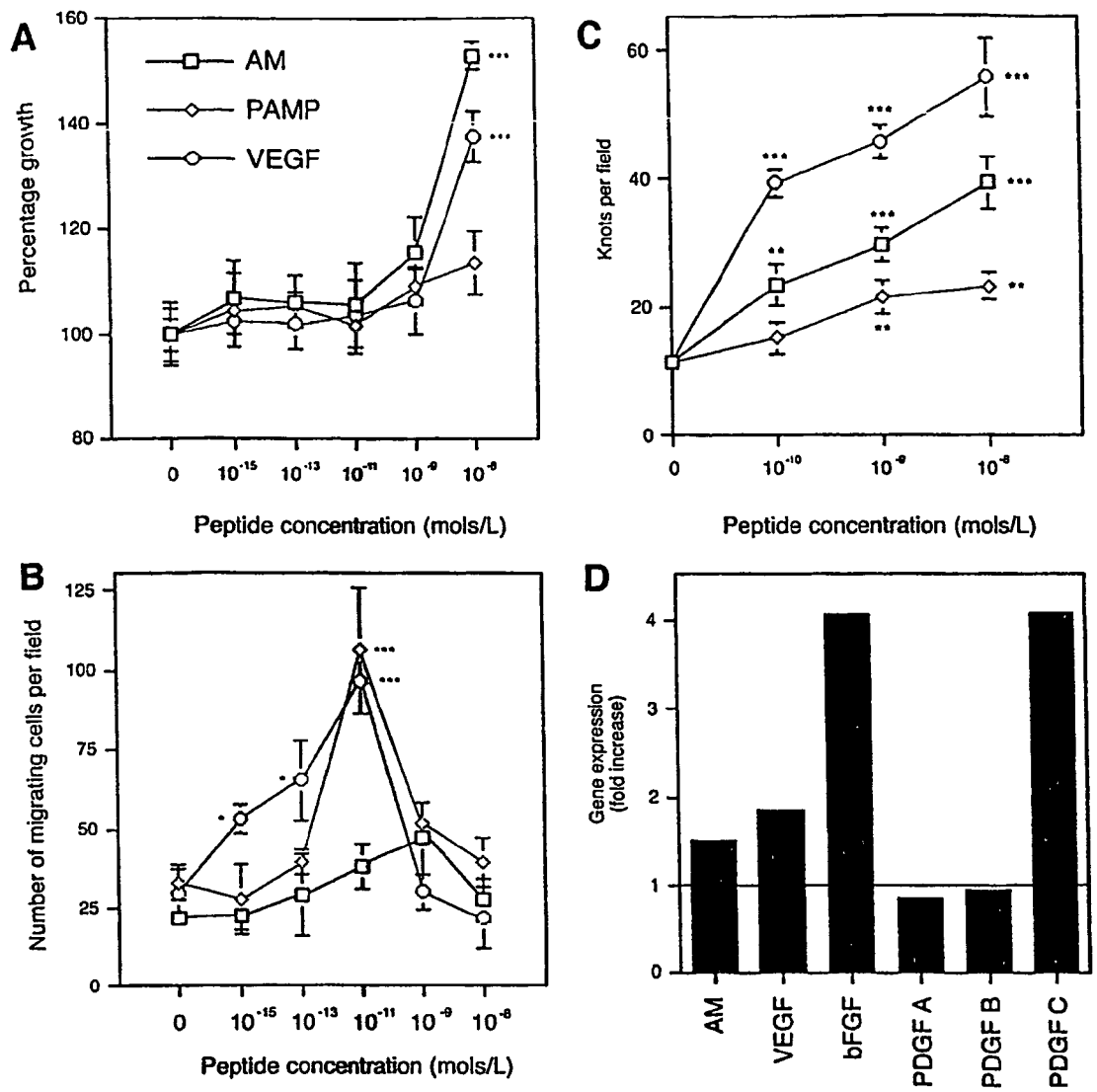
FIG. 6A-D is a set of graphs showing the influence of AM, VEGF, and PAMP in the physiology of endothelial cells.

For angiogenesis to occur, endothelial cells have to proliferate, migrate into new locations, and organize themselves into solid cords that eventually will develop into hollow tubes. All these processes are promoted by proangiogenic substances and all proangiogenic molecules must elicit at least one of these physiological actions. To investigate which of these phenomena are induced by PAMP, human microvascular endothelial cells were exposed to increasing concentrations of PAMP, AM, and VEGF and their effects on growth were compared (FIG. 6A), migration (FIG. 6B), and cord formation (FIG. 6C).

Endothelial cell growth analysis showed that AM and VEGF are able to significantly increase proliferation over the control at a concentration of $10^{-8}$ M ($p<0.001$ for both). On the other hand, PAMP did not significantly modify cell growth at the concentrations tested (FIG. 6A).

When migration of endothelial cells towards wells containing diverse concentrations of the peptides was tested, the behavior of the three molecules had an altogether different pattern. This time, AM did not modify cell migration significantly on the concentration range tested, whereas both VEGF and PAMP produced a four-fold increase in migration at a concentration of $10^{-11}$ M ($p<0.001$ for both). As has been previously reported for VEGF, both molecules showed a peak of migration stimulation with concentrations lower and higher than $10^{-11}$ M being less efficient. Interestingly, this peak was more pronounced for PAMP, since other VEGF concentrations, lower than $10^{-11}$ M, also induced a significant increase in cell migration (FIG. 6B).

Also tested was the ability of AM, VEGF, and PAMP to induce cord formation in a matrigel assay. The three molecules were able to induce cord formation in a dose-dependent manner. VEGF was the most efficient substance, followed by AM, while PAMP has a modest effect on this assay (FIG. 6C).

In addition, whether exogenously added PAMP had any influence in gene expression for other proangiogenic molecules was also investigated (FIG. 6D). Real time PCR experiments showed that PAMP mostly induces the expression of its own gene (AM), about 50% over basal levels. PAMP was also capable of elevating the expression of VEGF, bFGF, and PDGF C. Conversely, no significant modification in the expression of PDGF A or PDGF B was observed. (FIG. 6D). It was also investigated whether addition of 10 nM AM or VEGF had any effect on the expression of the AM/PAMP gene, but the values obtained for the treated endothelial cells were undistinguishable from the untreated controls.

E. A PAMP Antagonist Inhibits Angiogenesis In Vivo

Figure 7:
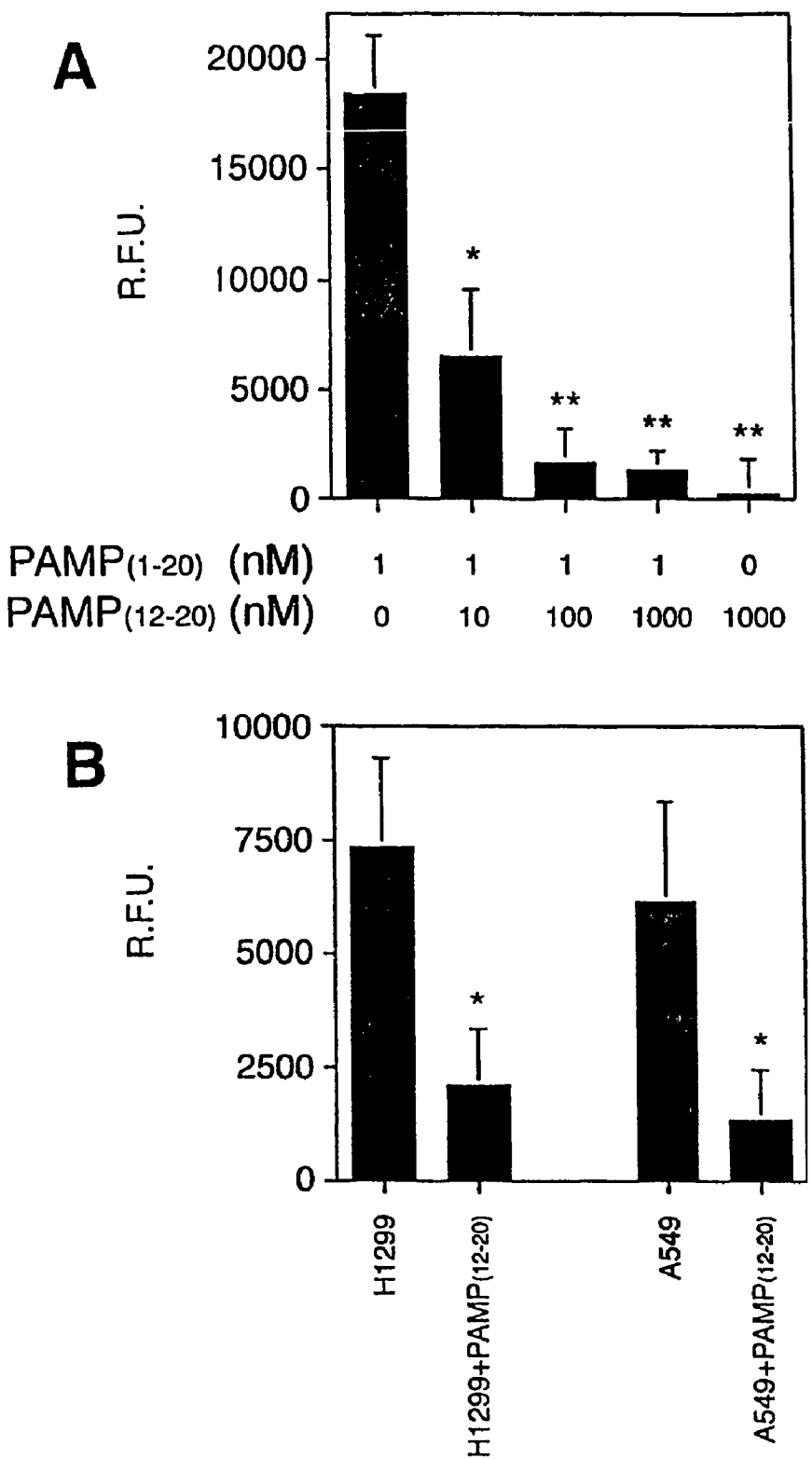
FIG. 7A-B is a pair of graphs showing the characterization of PAMP(12-20) as an inhibitor of PAMP-induced angiogenesis (FIG. 7A) Different concentrations of full-length PAMP and PAMP(12-20) were added to angioreactors and inserted under the skin of nude mice following the DIVAA protocol as indicated. Each bar represents the mean and standard deviation of six independent measurements. Statistical differences with PAMP alone (first bar) are represented as * ($p<0.05$) or ($p<0.01$).

Since the data demonstrate that PAMP is a potent promoter of angiogenesis, the inhibition of PAMP may result in reduced angiogenesis which could be beneficial in managing tumor growth. Since the peptide fragment PAMP(12-20) acts as a PAMP-receptor antagonist in endothelial cells, the ability of this peptide to inhibit angiogenesis was tested in vivo. First, the competition between synthetic full-length PAMP at 1 nM concentration and increasing doses of PAMP(12-20) was investigated using the DIVAA assay. A dose-dependent inhibition of the angiogenic response elicited by PAMP was observed (FIG. 7A). A hundred-fold excess of the peptide fragment (100 nM) inhibited angiogenesis to the basal levels obtained in the control (first bar in FIG. 7A). The peptide fragment by itself did not modify basal angiogenesis (last bar in FIG. 7A).

Since tumor cells produce many angiogenic factors (Chlenski et al., *Cancer Lett.* 197, 47-52, 2003), the contribution of PAMP to the total angiogenic response was investigated. Two human non-small cell lung cancer cell lines (A549 and H 299) were embedded in matrigel and placed in the DIVAA assay. Both cell lines induced an angiogenic response (FIG. 7B) that was completely blocked by 100 nM PAMP(1-20), indicating that PAMP signaling is somehow necessary for initiating angiogenesis.

Figure 8:
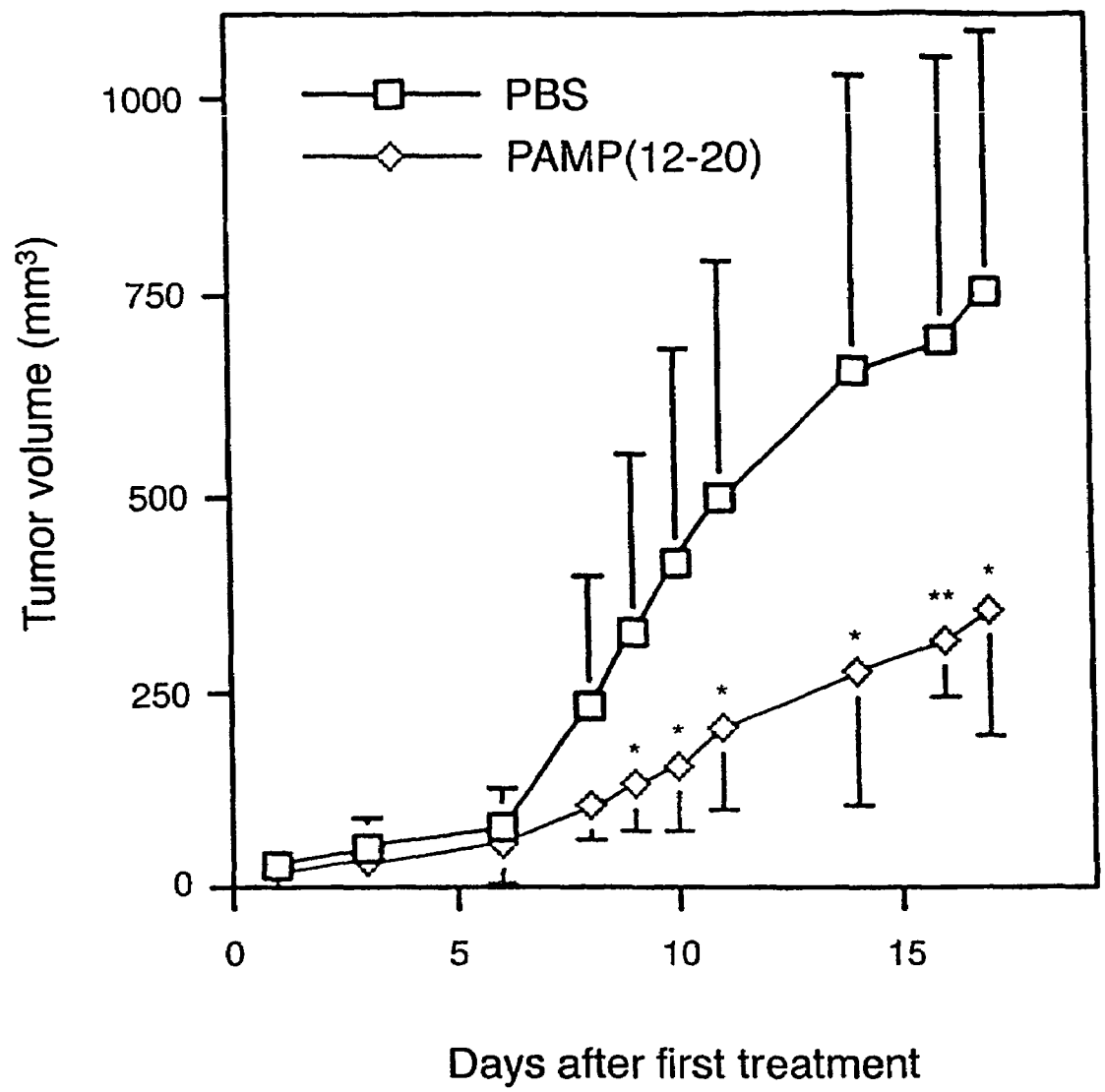
FIG. 8 is a graph showing the antitumor effect of PAMP (12-20) in a xenograft model. Athymic nude mice carrying A549 tumors were treated with either PBS (squares) or 1 mM PAMP(12-20) (diamonds). Each point represents the mean and standard deviation of ten mice. Statistical differences of tumor volume between treatments are represented by asterisks. *: $p<0.05$; **: $p<0.01$.

The previous data strongly suggest that inhibition of PAMP may be useful as an antitumoral therapy. To demonstrate whether this is true, a xenograft experiment was carried out. The human cell line A549 was injected under the skin of athymic nude mice and, two weeks later, all animals developed palpable tumor masses at the injection site. These mice were divided into two homogeneous groups and each set received a different treatment three times a week. The control group was treated with the vehicle (PBS) and the tumor mass kept increasing until the mice had to be sacrificed 18 days after treatment began (FIG. 8, squares). In contrast, the mice that received 1 mM PAMP(12-20) showed a slower rate of tumor growth (FIG. 8, diamonds). Statistical differences in tumor size between the groups were observed after nine days of treatment.

F. Discussion

Thus, the AM gene-related peptide PAMP is a potent angiogenic factor that is active at concentrations 6 orders of magnitude lower than previously recognized angiogenic molecules such as AM and VEGF. In addition, a receptor for PAMP is present in human endothelial cells and these cells react to the presence of PAMP by increasing their migration and cord formation potential, at the same time that expression for other angiogenic factors is boosted. In addition, the peptide fragment PAMP(12~20) acts as an angiogenesis antagonist notwithstanding whether neovascularization was induced by synthetic PAMP or by tumor cells, providing a new therapeutic approach to tumor management, as shown by the results in the xenograft model.

Example 3

Generation of Function-Blocking Anti-PAMP Antibodies

A function-blocking (function-neutralizing) purified polyclonal antibody is created in the following manner. One milligram (1 mg) PAMP peptide, or portion of a PAMP peptide, and 1 mg keyhole limpet hemocyanin (KLH) are mixed in 1 ml PBS. Ten µl of 25% glutaraldehyde (Sigma) is added to the mixture, which becomes flocular. The mixture is then added to 1 ml Complete Freund's Adjuvant and emulsified.

The host animal (usually a mouse or a rabbit) is challenged subcutaneously with 100 µl of the mixture. The challenge is repeated every two weeks, however the mixture is made with Incomplete Freund's Adjuvant for repeat challenges. Challenges are repeated three times for mice, at which time the animals are sacrificed. For rabbits, challenges continue every two weeks indefinitely.

The determination that an antibody specifically detects its target protein is made by any one of a number of standard inamunoassay methods; for instance, the Western blotting technique (Sambrook et al., In *Molecular Cloning: A Laboratory Manual*, CSHL, New York, 1989).

The determination that an antibody specifically blocks PAMP angiogenesis activity is made by any one of a number of standard angiogenesis bioassays, such as the cornea pocket assay (for example, Kenyon et al., *Invest Opthalmol. Vis. Sci.* 37:1625, 1996; Gaudric et al. *Ophthal Res.* 24: 181, 1992), the CAM assay (see Wilting et al, *Anat. Embryol.* 183: 259, 1991), the chick or rat aortic ring model, (for example, see Lichtenberg et al., *Pharmacol Toxicol.* 84: 34, 1999), the Directed in vivo Angiogenesis Assay (DIVAA; Martinez et al., *J. Natl. Cancer Inst*, 21;94(16):1226-37, 2002; see Example 1), or the embryonic chick aortic ring assay (for example, see Isaacs, et al., *J. Biol. Chem.*, 16;277(33):29936-44, 2002; Martinez et al., *J. Natl. Cancer Inst.*, 21;94(16): 1226-37, 2002).

PAMP is an arginine amide-modified peptide. As such, it is very resistant to carboxy peptidase, and the arginine amide modification conveys receptor recognition. Thus, antibodies made against the amide modification can target other amide-modified peptides, such as glucagon-like peptide-1 (GLP-1). Thus, hybridomas should be selected that do not react with GLP-1 or other amide-modified peptides, to avoid undesired side effects during treatment.

Example 4

Identification of PAMP Inhibitors

The following example describes a method that can be used to identify small molecule inhibitors of PAMP.

A function-blocking anti-PAMP antibody (see Example 3) is tested in an ELISA-type assay for specificity of binding to PAMP; this provides a baseline in vitro test for specific binding to PAMP. A library of molecules of potential interest (for example, a library of small molecule compounds, compounds generated from a combinatorial library, previously identified drug candidates, and so forth) is then screened in vitro for disruption of PAMP-antibody binding.

Molecules that disrupt specific antibody binding to PAMP can then be screened in an angiogenesis bioassay (in vitro or in vivo) for anti-angiogenesis or super-angiogenic activity, and thus the ability to block or super-agonize PAMP biological activity. Examples of angiogenesis bioassays include the cornea pocket assay (for example, Kenyon et al., *Invest Opthalmol. Vis. Sci.* 37:1625, 1996; Gaudric et al. *Ophthal. Res.* 24: 181, 1992), the CAM assay (see Wilting et al., *Anat. Embryol.* 183: 259, 1991), the rat aortic ring model, (for example, see Lichtenberg et al., *Pharmacol Toxicol.* 84: 34, 1999), the Directed in vivo Angiogenesis Assay (DIVAA; Martinez et al., *J. Natl. Cancer Inst.*, 21;94(16):1226-37, 2002; see Example 1), or the embryonic chick aortic ring assay (for example, see Isaacs, et al., *J. Biol. Chem.*, 16;277 (33):29936-44, 2002; Martinez et al., *J. Natl. Cancer Inst.*, 21;94(16):1226-37, 2002). Molecules that are found to block or super-agonize PAMP activity can then be subject to further characterization, for instance to determine their specificity, potency, and other relevant characteristics.

It will be apparent that the precise details of the methods or compositions described may be varied or modified without departing from the spirit of the described disclosure. We claim all such modifications and variations that fall within the scope and spirit of the claims below.

We claim:

1. A method of inducing or promoting angiogenesis:
   (a) in a tissue, the method comprising:
   introducing into the tissue an effective amount of the peptide of SEQ ID NO: 4 or a variant or fragment thereof that has at least 95% sequence identity with SEQ ID NO: 4 and that retains angiogenic activity, thereby inducing angiogenesis in the tissue, or
   (b) in a target area in a subject where angiogenesis is desired, the method comprising:
   introducing into the target area a therapeutically effective amount of the peptide of SEQ ID NO: 4 or a variant or fragment thereof that has at least 95% sequence identity with SEQ ID NO: 4 and that retains angiogenic activity, thereby promoting angiogenesis in the target area in the subject.

2. The method of claim 1, wherein the peptide comprises the amino acid sequence shown in SEQ ID NO: 4.

3. The method of claim 1, wherein the tissue comprises a graft, heart tissue, a blood vessel, a wound, or a coronary artery.

4. The method of claim 3, wherein the graft comprises a skin or organ graft.

5. The method of claim 1, wherein introducing comprises local administration or systemic administration.

6. The method of claim 5, wherein local administration comprises topical administration, intra-arterial administration, intravenous administration, subcutaneous administration, intramuscular administration, intrathecal administration, intrapericardial administration, intra-ocular administration, topical ophthalmic administration, or administration by inhalation.

7. The method of claim 1, wherein inducing angiogenesis comprises inducing neovascularization.

8. The method of claim 1(b), wherein the subject has or is at risk for developing coronary artery disease, peripheral vascular disease, cerebral ischemia, or a wound.

9. The method of claim 1(b), wherein the target area comprises a vessel in which blood flow is restricted.

10. The method of claim 1(b), wherein the subject has coronary artery disease, peripheral vascular disease, or a wound.

* * * * *

UNITED STATES PATENT AND TRADEMARK OFFICE
CERTIFICATE OF CORRECTION

| | |
|---|---|
| PATENT NO. | : 7,462,593 B2 |
| APPLICATION NO. | : 10/529116 |
| DATED | : December 9, 2008 |
| INVENTOR(S) | : Cuttitta et al. |

It is certified that error appears in the above-identified patent and that said Letters Patent is hereby corrected as shown below:

<u>On the Title Page</u>:

Page 1, Item (56) under Other Publications, "NH2-termainal" should read --NH$_2$-terminal--.

Page 1, Item (56) under Other Publications, "Gelantinases" should read --Gelatinases--.

Page 2, Item (56) under Other Publications, "Adrenomedulling" should read --Adrenomedullin--.

In column 2, lines 34-35, "for use in treating retinopathy" is a repeated phrase that should be deleted.

In column 3, line 19, "$p<0.001$" should read --$p<0.001$.--.

In column 3, line 47, "$0.01p>0.001$" should read --$0.01>p>0.001$--.

In column 3, line 56, "angiogenesis" should read --angiogenesis.--.

In column 4, lines 35-41, "PGDF" should read --PDGF--.

In column 4, lines 42-43, "18 5 RNA" should read --18 S RNA--.

In column 4, line 42, "prier" should read --primer--.

In column 6, line 2, "Opthalmol." should read --Ophthalmol.--.

In column 7, line 39, "compliment" should read --complement--.

In column 7, line 51, "complimentary" should read --complementary--.

In column 7, line 56, "membrances" should read --membranes--.

In column 8, line 19, "arthritis considered" should read --arthritis is considered--.

UNITED STATES PATENT AND TRADEMARK OFFICE
CERTIFICATE OF CORRECTION

PATENT NO.         : 7,462,593 B2
APPLICATION NO.    : 10/529116
DATED              : December 9, 2008
INVENTOR(S)        : Cuttitta et al.

It is certified that error appears in the above-identified patent and that said Letters Patent is hereby corrected as shown below:

In column 9, line 27, "tansyocardial" should read --transmyocardial--.

In column 22, line 19 (in Table 1), "Orignal" should read --Original--.

In column 22, line 48, "leucyl isoleucyl" should read --leucyl, isoleucyl--.

In column 22, line 52, "glutamnyl" should read --glutamyl--.

In column 24, line 7, "three dimensional" should read --three-dimensional--.

In column 24, line 21, "*Munson*" should read --Munson--.

In column 24, line 21, "Pharmacology Munson" should read --Pharmacology, Munson--.

In column 25, line 1, "described GFP" should read --described for GFP--.

In column 25, line 3, "interest When" should read --interest. When--.

In column 25, line 9, "western blots" should read --Western blots--.

In column 25, lines 44-45, "a defined periods" should read --a defined period--.

In column 26, line 12, "characteization" should read --characterization--.

In column 27, line 2, "Marinastat" should read --Marimastat--.

In column 27, line 35, "sublingual oral" should read --sublingual, oral--.

In column 27, line 54, "mirocapsules" should read --microcapsules--.

In column 27, line 60, "intra-arterial intramuscular" should read --intra-arterial, intramuscular--.

In column 30, line 9, "Non-queous" should read --Non-aqueous--.

In column 30, line 60, "press" should read --Press--.

UNITED STATES PATENT AND TRADEMARK OFFICE
CERTIFICATE OF CORRECTION

| | |
|---|---|
| PATENT NO. | : 7,462,593 B2 |
| APPLICATION NO. | : 10/529116 |
| DATED | : December 9, 2008 |
| INVENTOR(S) | : Cuttitta et al. |

It is certified that error appears in the above-identified patent and that said Letters Patent is hereby corrected as shown below:

In column 30, line 64, "effect" should read --affect--.

In column 31, line 5, "1988);" should read --1988;--.

In column 31, line 6, "1989);" should read --1989;--.

In column 31, line 37, "trascutaneous" should read --transcutaneous--.

In column 32, line 3, "ad administered" should read --administered--.

In column 32, line 9, "admniistered" should read --administered--.

In column 33, lines 66-67, "peptido-encoding" should read --peptide-encoding--.

In column 34, line 49, "100μl mouse" should read --100μl per mouse--.

In column 34, line 53, "placed an eppendorf" should read --placed in an Eppendorf--.

In column 35, line 46, "13 day-old" should read --13-day-old--.

In column 35, line 62, "DLVAA" should read --DIVAA--.

In column 35, line 63, "Am. ]." should read --Am. J.--.

In column 35, line 64, "143 1-1439" should read --1431-1439--.

In column 36, line 16, "ATTC" should read --ATCC--.

In column 36, line 26, "molecular" should read --Molecular--.

In column 37, line 24, "reaction" should read --reaction.--.

In column 37, lines 42-45, "PGDF" should read --PDGF--.

In column 37, line 57, "19" should read --19)--.

In column 37, line 59, "18 5 RNA" should read --18 S RNA--.

UNITED STATES PATENT AND TRADEMARK OFFICE
CERTIFICATE OF CORRECTION

| | | |
|---|---|---|
| PATENT NO. | : 7,462,593 B2 | |
| APPLICATION NO. | : 10/529116 | |
| DATED | : December 9, 2008 | |
| INVENTOR(S) | : Cuttitta et al. | |

It is certified that error appears in the above-identified patent and that said Letters Patent is hereby corrected as shown below:

In column 38, line 32, "Am. ]." should read --Am. J.--.

In column 38, lines 45-46, "compared to and VEGF" should read --compared to AM and VEGF--.

In column 38, line 62, "20 19-2028" should read --2019-2028--.

In column 39, lines 21-23, "their effects on growth were compared (FIG. 6A), migration (FIG 6B), and cord formation (FIG 6C)." should read --their effects on growth (FIG. 6A), migration (FIG 6B), and cord formation (FIG 6C) were compared--.

In column 39, line 57, "undistinguishable" should read --indistinguishable--.

In column 40, line 43, "(12~20)" should read --(12-20)--.

In column 41, line 3, "inamunoassay" should read --immunoassay--.

In column 41, line 9, "Opthalmol." should read --Ophthalmol.--.

In column 42, line 16, "Opthalmol." should read --Ophthalmol.--.

Signed and Sealed this

Twenty-first Day of April, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,462,593 B2  Page 1 of 1
APPLICATION NO. : 10/529116
DATED : December 9, 2008
INVENTOR(S) : Cuttitta et al.

It is certified that error appears in the above-identified patent and that said Letters Patent is hereby corrected as shown below:

On the Title Page, item (73) Assignee: insert the following:

--The Government of the United States of America as represented by the Secretary of the Department of Health and Human Services--

Signed and Sealed this

Twenty-seventh Day of July, 2010

David J. Kappos
*Director of the United States Patent and Trademark Office*